(12) United States Patent
Bahatt et al.

(10) Patent No.: US 8,139,213 B2
(45) Date of Patent: *Mar. 20, 2012

(54) TWO-DIMENSIONAL SPECTRAL IMAGING SYSTEM

(75) Inventors: Dar Bahatt, Foster City, CA (US); Chirag Patel, Foster City, CA (US); Roy H. Tan, Union City, CA (US); Derek Prothro, San Francisco, CA (US)

(73) Assignee: Life Technologies Corporation, Carlsbad, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/389,292

(22) Filed: Feb. 19, 2009

(65) Prior Publication Data

US 2010/0039642 A1    Feb. 18, 2010

Related U.S. Application Data

(63) Continuation of application No. 11/480,287, filed on Jun. 30, 2006, now Pat. No. 7,663,750, which is a continuation of application No. 11/479,962, filed on Jun. 30, 2006.

(60) Provisional application No. 60/696,301, filed on Jun. 30, 2005, provisional application No. 60/817,833, filed on Jun. 29, 2006.

(51) Int. Cl.
*G01J 3/28* (2006.01)

(52) U.S. Cl. .......................................... 356/328

(58) Field of Classification Search .......... 356/402–425, 356/328
See application file for complete search history.

(56) References Cited

U.S. PATENT DOCUMENTS

| | | | |
|---|---|---|---|
| 4,375,919 A | 3/1983 | Busch | |
| 4,494,872 A | 1/1985 | Busch | |
| 4,811,218 A | 3/1989 | Hunkapiller et al. | |
| 5,159,199 A * | 10/1992 | LaBaw | 250/339.02 |
| 5,355,215 A | 10/1994 | Schroeder et al. | |
| 5,483,075 A | 1/1996 | Smith et al. | |
| 5,498,324 A | 3/1996 | Yeung et al. | |
| 5,543,026 A | 8/1996 | Hoff et al. | |
| 5,731,874 A | 3/1998 | Maluf | |
| 5,800,996 A | 9/1998 | Lee et al. | |
| 5,846,489 A * | 12/1998 | Bienhaus et al. | 422/63 |
| 5,854,684 A | 12/1998 | Stabile et al. | |
| 5,872,623 A | 2/1999 | Stabile et al. | |
| 6,017,434 A | 1/2000 | Simpson et al. | |
| 6,097,025 A | 8/2000 | Modlin et al. | |
| 6,100,974 A | 8/2000 | Reininger | |

(Continued)

FOREIGN PATENT DOCUMENTS

WO    WO2005/028109    3/2005

OTHER PUBLICATIONS

"Observation of Surface Objects, Importance of the slit in the case of surface objects", http://www.astrosurf.com/buil/us/spectro8/spaude4_us.htm, Nov. 1, 2006, 7 pgs.

(Continued)

*Primary Examiner* — Tarifur Chowdhury
*Assistant Examiner* — Abdullahi Nur

(57) ABSTRACT

Systems, including methods, apparatus, and algorithms, for spectrally imaging a two-dimensional array of samples.

12 Claims, 15 Drawing Sheets

U.S. PATENT DOCUMENTS

| | | | |
|---|---|---|---|
| 6,495,818 | B1 | 12/2002 | Mao |
| 6,690,467 | B1 | 2/2004 | Reel |
| 6,759,235 | B2 | 7/2004 | Empedocles et al. |
| 7,009,699 | B2 | 3/2006 | Wolleschensky et al. |
| 7,663,750 | B2 | 2/2010 | Bahatt et al. |
| 7,817,273 | B2 | 10/2010 | Bahatt et al. |
| 2003/0054740 | A1 | 3/2003 | Mansky |
| 2003/0210469 | A1 | 11/2003 | Boege |
| 2003/0223059 | A1* | 12/2003 | Li ........................ 356/317 |
| 2004/0182710 | A1 | 9/2004 | Tanaami |
| 2007/0059754 | A1 | 3/2007 | Kordunsky et al. |

OTHER PUBLICATIONS

"Sprial Spectrograph" Spectrograph Image, http://www.ast.cam.ac.uk/~optics/sprial/images/lightpath.gif, 1 pg.

"What Are Astronomers Doing? Marcario Low Resolution Spectrograph", (2004) *McDonald Observatory of the University of Texas at Austin*: Accessed Nov. 1, 2006 http://mcdonaldobservatory.org/research/instruments/instruments.php:i_id=18, 1 pg.

"Sprial Spectrograph", (1997) Institute of Astronomy, University of Cambridge; *Institute of Astronomy, University of Cambridge*; http://www.ast.cam.ac.uk/~op-tics/spiral.htm, 4 pgs.

Cornet, P. et al., "Conical diffraction of a plane wave by an inclined parallel-plate grating", vol. 14, No. 2, Feb. 1997, *J. Opt. Soc. Am. A*, Mar. 1997, 437-449.

Gavin, Maurice, "WPO-Lo Res lunar spectrograph", (Sep. 2001) http://home.freeuk.com/m.gavin/lunaspec.htm, 1 pg.

Gavin, Maurice, "WPO-Split Field Spectrograph for SNe confirmation", (2001); Accessed Nov. 1, 2006; http://home.freeuk.com/m.gavin/snspect.htm, 3 pgs.

Gavin, Maurice, "WPO-Review of the Rainbow Optics grating + grating efficiency", (2005) http://www.astroman.fsnet.co.uk/rainbow.2.htm.

Lerner, J.M. et al., "*The Optics of Spectroscopy*", Mar. 27, 2002, 61 pgs.

"Space Telescope Imaging Spectrograph Instrument Handbook for Cycle 12", Version 6.0; (2002) Space Telescope Science Institute; Accessed Nov. 1, 2006; http://www.stsci.edu/hst/stis/documents/handbooks/cycle12/c12_special2.html.

* cited by examiner

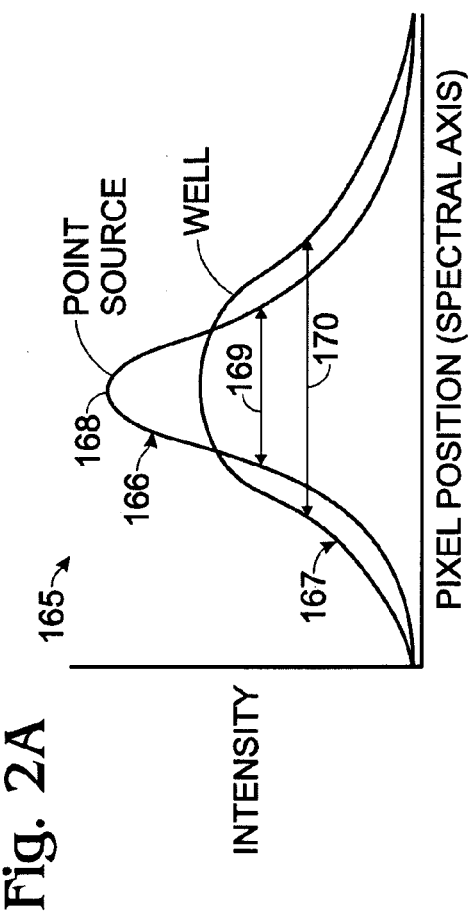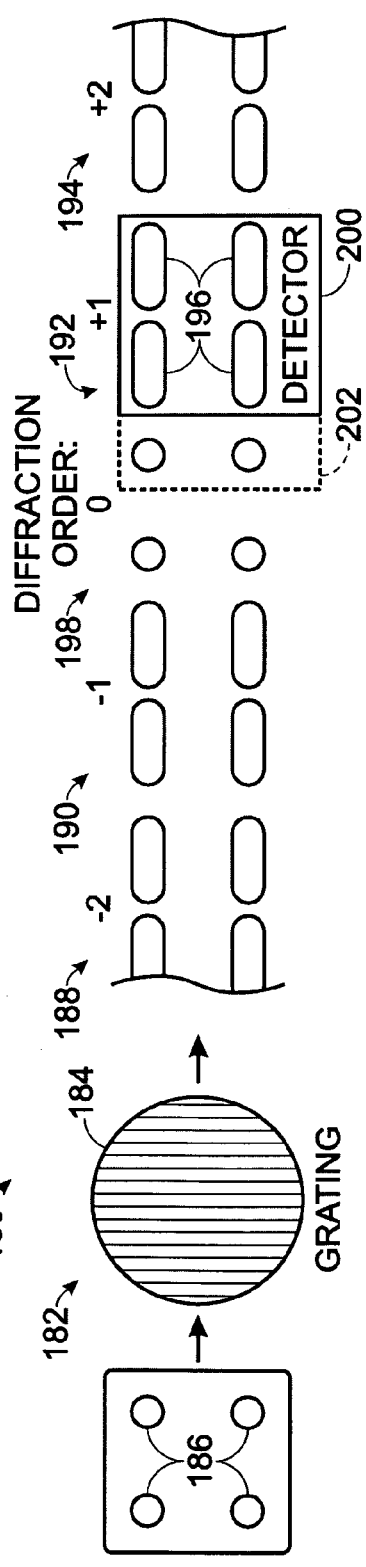

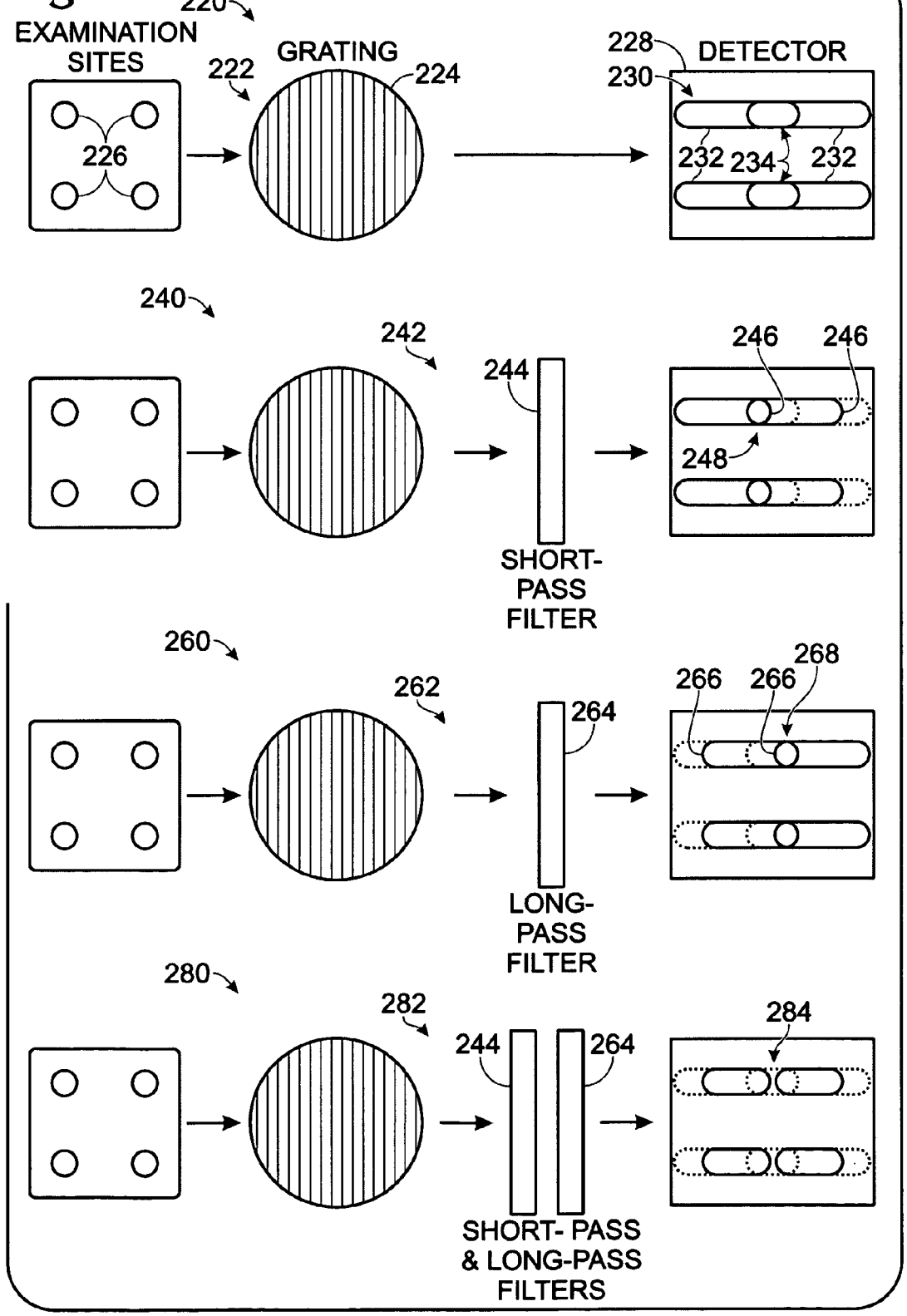

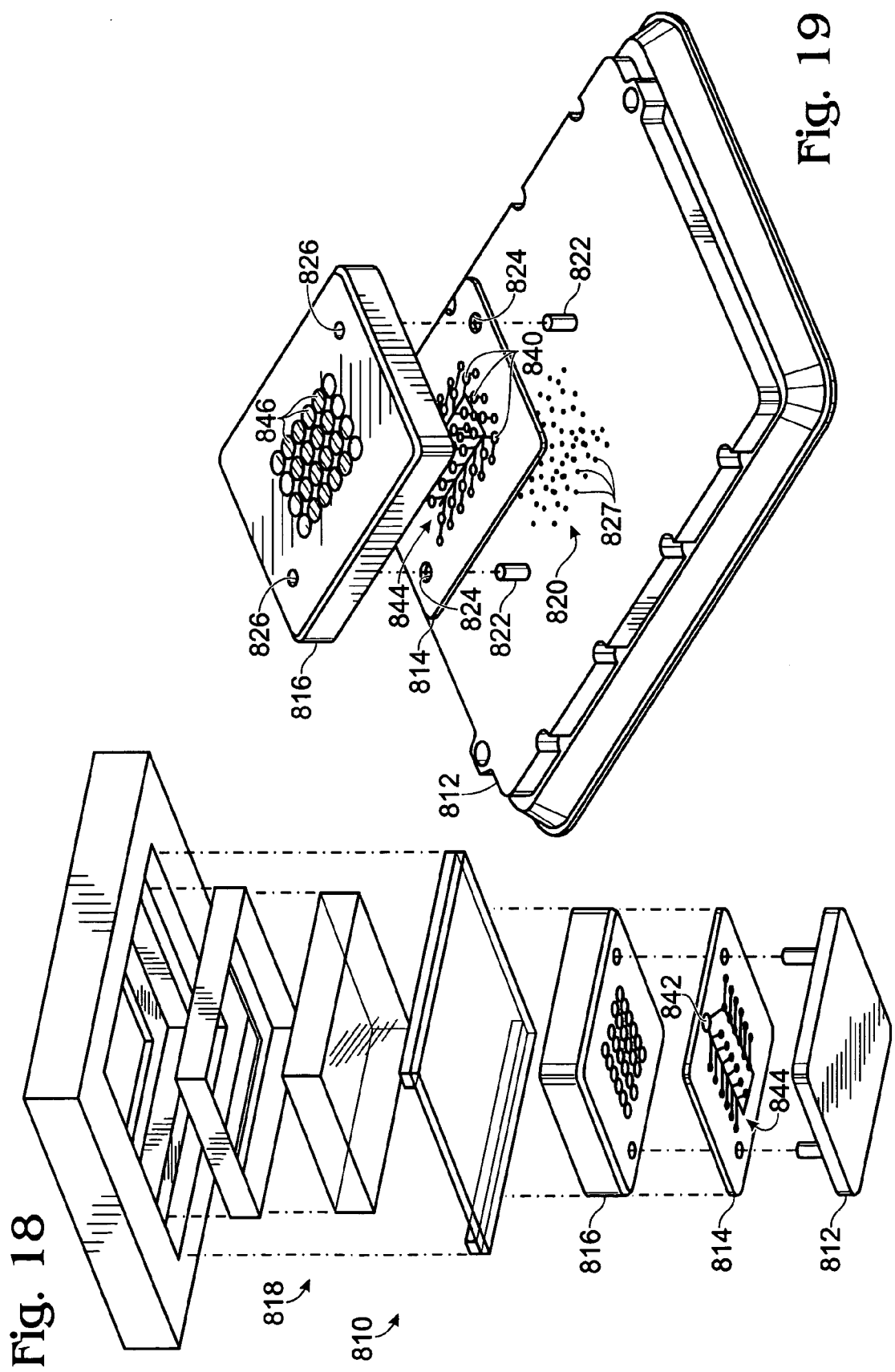

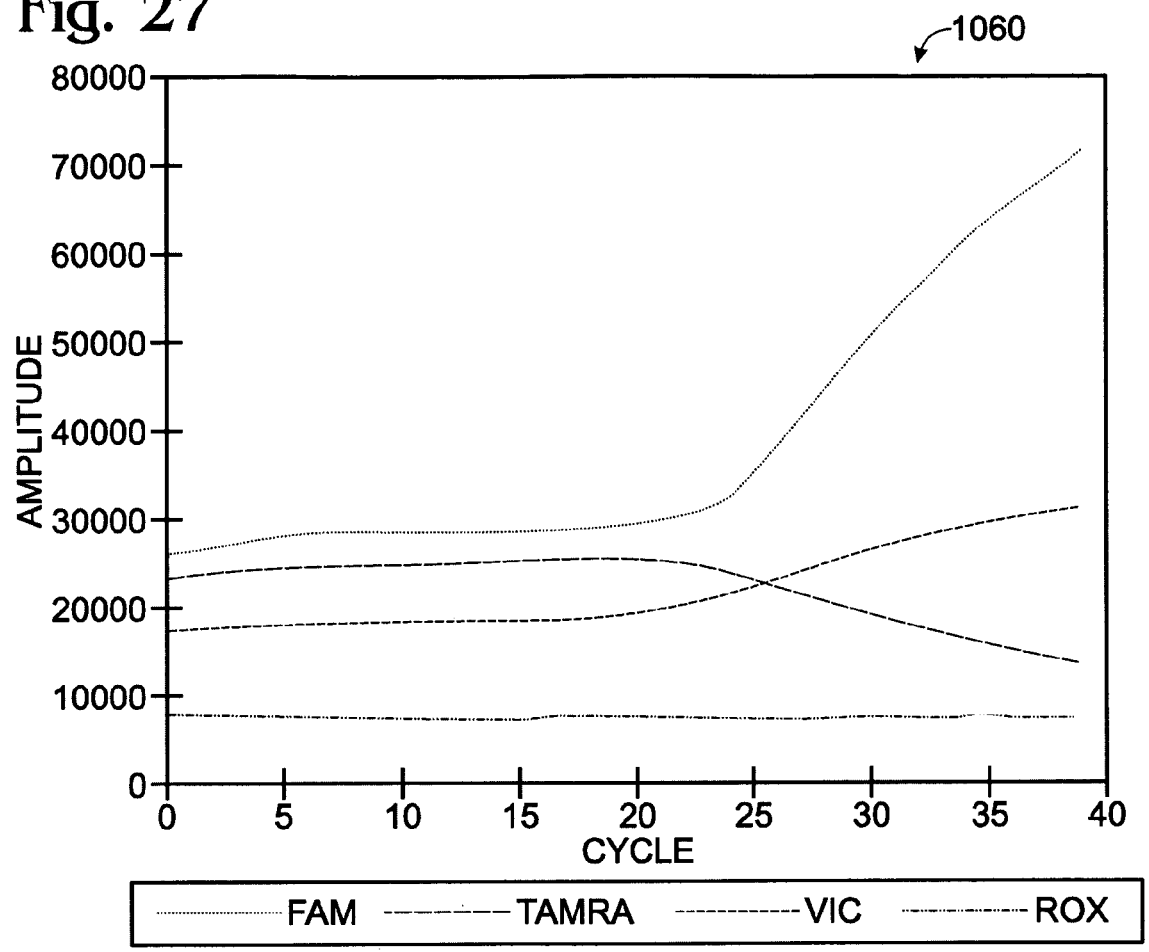

TWO-DIMENSIONAL SPECTRAL IMAGING SYSTEM

CROSS-REFERENCES

This application claims priority under 35 U.S.C. §119(e) to Provisional Application No. 60/696,301, filed Jun. 30, 2005; Provisional Application No. 60/817,833, filed Jun. 29, 2006; and is a continuation of application Ser. No. 11/480,287, filed Jun. 30, 2006 and application Ser. No. 11/479,962, filed Jun. 30, 2006. Each of these patent applications are incorporated herein by reference in their entirety.

INTRODUCTION

The identity, amounts, properties, and/or interactions of samples, such as samples including biomolecules (biological samples), can be analyzed by detecting light emitted by the samples. The emitted light can be detected, and illumination optionally can be provided, by a suitable light-detection system. To facilitate analysis of multiple samples with the light-detection system, the samples can be disposed in an array defined by a sample holder. In some cases, more information about the samples can be obtained by measuring distinct spectral components of the light emitted by each sample in the array.

SUMMARY

The present teachings provide systems, including methods, apparatus, and algorithms, for spectrally imaging a two-dimensional array of samples.

BRIEF DESCRIPTION OF THE DRAWINGS

FIG. 2A is a graph of a pair of spectral profiles obtained from two-dimensional spectral images of the same spectral composition imaged in an examination site of a spectral imaging system as a point source or distributed across a well, in accordance with aspects of the present teachings.

FIG. 2B is a schematic view of selected portions of another exemplary spectral imaging system illustrating how an optical system of the imaging system resolves nondispersed and dispersed light from a two-dimensional array of examination sites, in accordance with aspects of the present teachings.

FIG. 3 is a schematic view of spectral imaging systems having various exemplary arrangements of optical relay structures including short-pass and/or long-pass filters, in accordance with aspects of the present teachings.

FIG. 18 is an exploded view of an exemplary examination assembly for positioning samples in an examination area of an exemplary spectral imaging system, viewed from generally below the assembly, in accordance with aspects of the present teachings.

FIG. 19 is an exploded view of selected portions of the examination assembly of FIG. 18, viewed from generally above the assembly.

FIG. 27 is a graph of the relative spectral contributions of the four indicated dyes to the composite spectra of the sample of FIG. 26 at the indicated cycle numbers during thermal cycling of the sample to promote amplification of nucleic acid template, if any, in the sample, in accordance with aspects of the present teachings.

DESCRIPTION OF VARIOUS EMBODIMENTS

Figure 1:
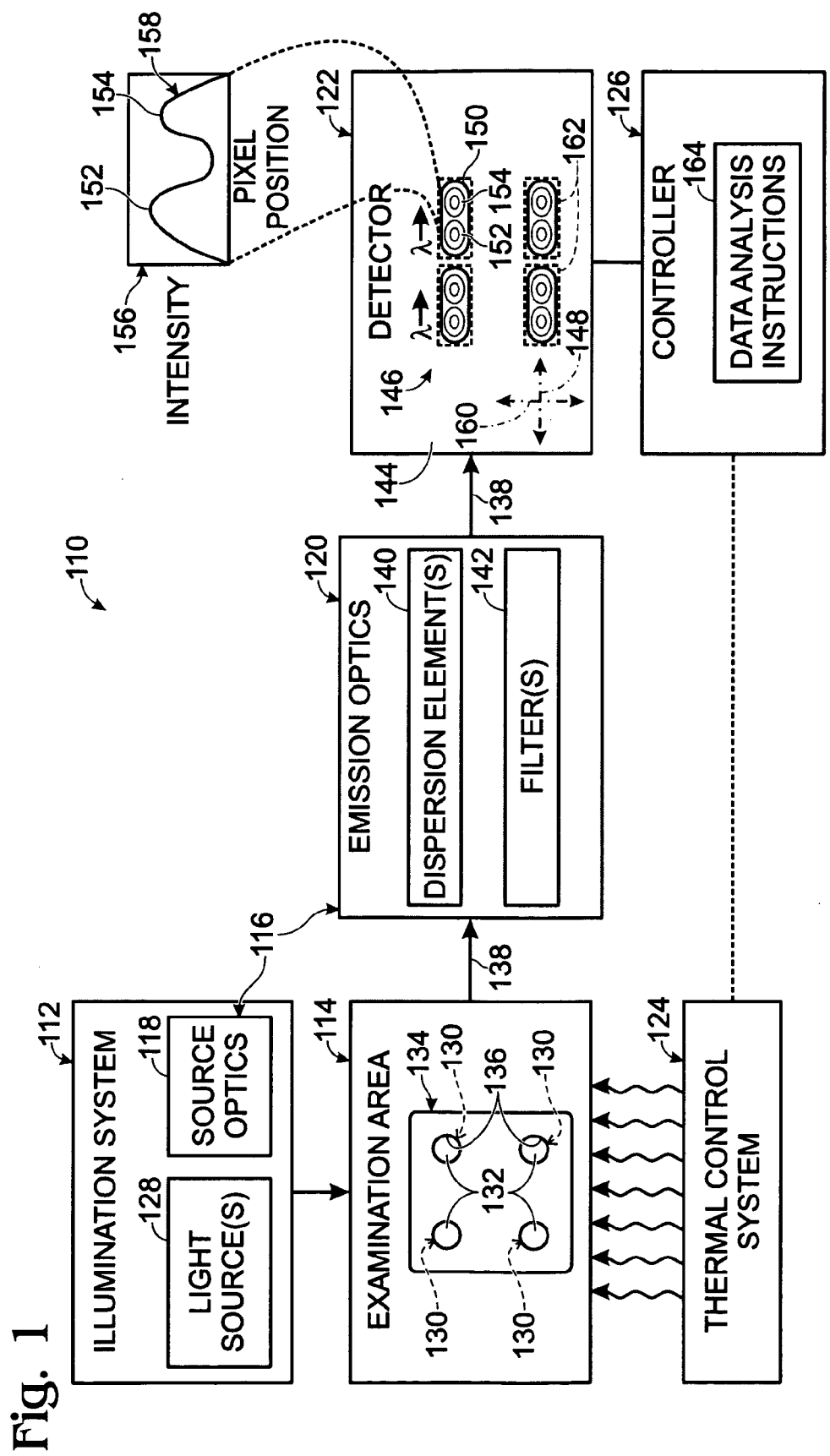
FIG. 1 is a schematic view of an exemplary spectral imaging system, in accordance with aspects of the present teachings.

The present teachings provide systems, including methods, apparatus, and algorithms, for spectrally imaging a two-dimensional array of samples.

The imaging systems described herein can include (1) an examination area including a two-dimensional array of examination sites, (2) an illumination system, (3) an optical system (with at least an output/emission optical relay structure), and/or (4) a light detector for imaging, among others. The illumination system can include one or more light sources that illuminate samples disposed in the examination sites, to induce light emission by the samples. The optical system (or an output optical relay structure thereof) can include at least one dispersion element, such as a grating, that disperses the emitted light, particularly visible light, from each sample into a corresponding spectrum. In addition, the optical system can direct the dispersed light onto a detection area of the detector such that a two-dimensional array of sample spectra (e.g., first order (+1 or −1) diffraction spectra) from the samples falls concurrently onto the detection area. In some examples, the array of spectra, collectively, can be at least substantially resolved from nondispersed (i.e., zero order) light from the samples, and, optionally, from higher order light, such as second diffraction order light from the samples. Accordingly, the optical system can include one or more filters, such as low-pass and/or high-pass filters that filter the emitted light, to truncate each spectrum at one or both ends. Selective truncation of spectra can enable the optical system to expand a selected wavelength region of each spectrum on the detector, for better resolution, while reducing crosstalk between adjacent spectra that would be present without filters. An overview of exemplary spectral imaging systems is presented below in Section I.

The systems also can include a sample holder configured to be positioned in the examination area. The sample holder can have wells that hold fluid. The wells can be open (uncovered) or the sample holder can include one or more sealing elements that seal each well after placement of fluid (e.g., sample) in the well. The sample holders can define sets of orthogonal axes along which the wells are disposed. In addition, the wells can be disposed in an array of aligned rows and columns or can have an offset relationship such that the wells are staggered. The optical system can define a dispersion axis that has any suitable relationship to the array of spectra. In some embodiments, the array of spectra can define a pair of orthogonal axes and the dispersion axis can be parallel to one of the orthogonal axes or oblique to both orthogonal axes. In some examples, an oblique spectral axis can offer a greater distance for extending spectra, to provide better resolution of spectral components and/or less optical crosstalk. Further aspects of sample holders and defining oblique spectral axes are described below, such as in Section III and Example 1, among others.

The methods can include calibrating a spectral imaging system to assign an array of regions of a detector corresponding to an array of examination sites. Calibration can include detecting light of known spectral composition from the examination sites. The light of known spectral composition can be provided from the examination sites, e.g., from isolated/pure/unconjugated dyes, illumination light, test samples, and/or the like. The methods also or alternatively can include obtaining and/or processing spectral data from samples based on the assigned regions of interest. In some examples, the assigned regions of interest can be moved based on detected signals from one or more fiducials provided by a sample holder. The fiducials can be one or more wells (e.g., to provide nondispersed light) and/or can be an optically detectable feature of the sample holder that is spaced from wells of the sample holder. Further aspects of calibrating spectral imaging systems and analyzing samples with calibrated systems are described below in Sections VIII and X, among others.

The methods also can include using a spectral imaging system to perform kinetic assays of two-dimensional sample arrays. Each sample spectrum can be monitored over time to determine a change, if any, in the spectrum. For example, each sample can include a plurality of reactions that are assayed and/or monitored over time by the spectral imaging system. In some examples, the reactions can include amplification of nucleic acids to allow detection and/or quantitation of one or more nucleic acids in each sample. Further aspects of assays that can be performed with spectral imaging systems are described elsewhere in the present teachings, such as in Section IX and in Example 9, among others.

The algorithms can be applied to image data collected by a spectral imaging system. In some examples, the algorithms can be used to calibrate a detector and/or to identify spectral data for individual samples. In some examples, the algorithms can, for example, reduce optical distortion in spectral image data. In some examples, the distortion can include stretching and/or curving of image data, among others. Alternatively, or in addition, the algorithms can select particular regions of spectral image data for processing such to provide software-based filtering of sample signals. Further aspects of algorithms that can be suitable for using in spectral imaging systems are described, for example, in Examples 7, 8, 11, and 12, and in the patent applications listed above under Cross-References, which are incorporated herein by reference.

Concurrent imaging of spectra from a two-dimensional array of samples can have a number of advantages. For example, concurrent imaging can save time and/or reduce mechanical complexities (such as vibrations, since it can obviate the need for changing spectral filters to determine emission wavelengths). Furthermore, concurrent imaging, in some examples, can allow analysis of faster kinetic assays, since data can be collected during a kinetic assay from different samples at the same time (or in rapid succession) without movement of mechanical parts, providing faster data acquisition and/or a better direct comparison between (or within) samples.

The following sections further describe these and other aspects of the present teachings, including (I) an overview of exemplary spectral imaging systems, (II) illumination systems, (III) examination areas and sample holders, (IV) optical systems, (V) detectors, (VI) controllers, (VII) thermal control systems, (VIII) calibration of spectral imaging systems and sample analysis, (IX) applications, and (X) examples, among others.

I. OVERVIEW OF EXEMPLARY SPECTRAL IMAGING SYSTEMS

FIG. 1 shows a schematic view of an exemplary two-dimensional spectral imaging system 110. System 110 can include an illumination system 112, an examination area 114, an optical system 116 (e.g., with respective input and output optical relay structures forming source optics 118 and emission optics 120) operatively coupled to the examination area, a light detector for imaging (an array detector) 122, a thermal control system 124, and a controller 126, among others. These and other devices, assemblies, and systems described in the present teachings can be used in any suitable combination and can be present any suitable number of times in a spectral imaging system.

The illumination system can include a light source 128 and source optics 118. The light source can produce light for excitation of samples disposed in the examination area, and the source optics can direct the light to the samples. In some examples, some or all of the optical elements of the illumination system can be integral to the light source. The illumination system can illuminate examination area 114, which can include a two-dimensional array of examination sites 130. Standards or samples 132 can be disposed in the examination area via a sample holder 134 having a plurality of compartments, such as wells 136, for positioning the standards or samples in the examination sites.

Light can be emitted from the examination sites, such as from luminophores (e.g., fluorophores) disposed in the wells. The emitted light can be directed to detector 122 by emission optics 120 forming a (linear or bent) optical path 138 between the examination sites and the detector. The emission optics can include at least one dispersion element 140 to spectrally disperse the emitted light. The emission optics also can include one or more filters 142 that selectively restrict passage of part of the emitted light according to wavelength. Furthermore, the emission optics can direct the dispersed light onto a detection area 144 of the detector such that a two-dimensional array 146 of spectra (also termed spectral images) of the two-dimensional array of examination sites falls concurrently on the detection area (if the sites are illuminated at the same time).

Each spectrum can be a spectrally dispersed image of emitted light from a corresponding examination site, such as an image of spectral light emitted from a sample disposed in an examination site. For example, in the present illustration, each spectral image of the contents of a circular well results from dispersion of light in a direction parallel to a spectral axis 148 defined by the emission optics of the system, to stretch each well image into a generally oval shape (with a sufficient spectral range of emitted light). The intensity within each spectrum can be determined by its spectral composition. For example, exemplary spectrum 150 includes a pair of intensity peaks 152, 154 at distinct pixel positions (and thus at different wavelengths or wavelength ranges) along a line parallel to the spectral axis. Graph 156 illustrates a simplified one-dimensional spectral profile 158 that can be produced by processing image data for spectrum 150, by collapsing the two-dimensional spectral data from spectrum 150 into a linear vector/profile. In particular, the image data for spectrum 150 can be summed in a direction parallel to a spatial axis 160 orthogonal to the spectral axis.

Each sample spectrum can be detected by a corresponding region of interest 162 of the detector (and/or obtained as a portion of image data from the detector). The region of interest also can be abbreviated as a region or "ROI" in the present teachings and is shown here as a dashed rectangle. Each region of interest can be assigned by calibration using data analysis instructions 164 (e.g., algorithms) of the controller prior to analysis of test samples (e.g., in conjunction with calibration standards disposed in the examination sites) and/or can be assigned or repositioned based on spectral images of the test samples themselves. The detector regions of interest can be elongate, with the length of each region disposed parallel to spectral axis 148 and the width of each spectrum region perpendicular to the spectral axis. The axes of the array of regions of interest can be aligned with orthogonal axes of the detector, as shown here, or the array can be angularly offset (i.e., slanted) on the detector. In some examples, image data from a slanted array of regions of interest can be processed to effectively rotate the image data relative to the matrix axes in which the image data is arranged. Such rotation of image data can facilitate further processing of the image data (such as collapsing two-dimensional image data in a direction(s) parallel to one or both orthogonal axes). Alternatively, or in addition, each region of interest can extend in a direction parallel to a spectral axis disposed obliquely to orthogonal axes defined by the detector and/or the array of spectral images (e.g., see Example 1). Further aspects of processing slanted image data are described in U.S. Provisional Patent Application Ser. No. 60/696,301, filed Jun. 30, 2005, which is incorporated herein by reference.

The size and shape of each region of interest for a particular system can be defined by the light source, sample configuration, luminophore(s) in the samples, and/or the optical system, among others. In some examples, these parameters can be adjusted such that the regions of interest for most or all of the samples do not overlap substantially with one another and also do not overlap substantially with adjacent higher order or lower order diffraction (or nondispersed (zero order)) regions. These parameters also can be adjusted such that the regions of interest (and thus the spectral images) are closely packed, which can provide more efficient use of the detector (e.g., faster data acquisition, higher signal-to-noise, etc.). For example, the width of each region of interest can be at least about the same as, or about two, five, or ten times greater than the lateral spacing (the gap) between the adjacent sides of laterally adjacent regions of interest. Alternatively, or in addition, the length of each spectrum region can be at least about the same as, greater than, and/or at least about two, five, or ten times greater than the longitudinal spacing (the gap) between the adjacent ends of longitudinally adjacent regions of interest. Further aspects of calibrating spectral imaging systems, collecting image data, processing the image data, interpreting the processed image data, and determining assay results from the processed image data are described elsewhere in the present teachings, such as in Sections VIII and X, among others, and in the patent applications listed above under Cross-References, which are incorporated herein by reference.

Thermal control system 124 can be operatively coupled to the examination area for controlling the temperature thereof. In some embodiments, the thermal control system can be configured for thermal cycling of the examination area and particularly a sample holder/wells disposed therein. The thermal cycling can be performed in an automated manner for one cycle or a plurality of cycles. In addition, a thermally conductive portion of the thermal control system can be configured to be in contact with the sample holder, for conductive heating and/or cooling thereof. Further aspects of thermal control systems are described elsewhere in the present teachings, such as in Section VII and in Example 6, among others.

The components of spectral imaging systems provided by the present teachings can, more generally, be selected and/or configured according to application, desired level of automation, and so on. For example, controller(s) 126 can be configured to control any suitable components of the system, including illumination system 112, examination area 114, optical system 116, detector 122, thermal control system 124, and/or the like. In chemiluminescence (including bioluminescence) applications, the imaging system can include the components indicated above, and/or other components, without the light source and/or source optics, or with the light source and/or source optics present but not used.

The spectral imaging system also can include additional components, such as (1) a sample-handling mechanism to convey samples and/or sample holders to and/or from the examination area, (2) a registration device to drive movement of the sample holder within the examination area, and/or (3) a sample-identification mechanism such as a barcode reader or a radiofrequency (RF)-tag reader to identify samples and/or sample holders, and optionally to configure or operate system components accordingly, among others.

FIG. 2A shows a graph 165 of a pair of one-dimensional spectral profiles 166, 167 obtained from two-dimensional spectral images of the same spectral composition imaged in an examination site of a spectral imaging system. Narrower spectral profile 166 can be produced from a sample configured as a point (or line) source, such as spotted in a very small area (as on a biochip), restricted to a very small volume (such as in or on bead), imaged with an aperture of small size, and/or occupying a small portion of the field of view, among others. Broader spectral profile 167 can be produced from the same sample distributed across an area or in a volume of significant size for the optical arrangement of the system, such that the sample does not act as a point (or line) source. In particular, the sample can be disposed in a sample holder of the imaging systems described herein. The sample holder can have wells large enough to substantially affect the shape of the resulting spectrum detected. For example, spectral profile 167 can be broadened substantially in directions parallel to the spectral axis relative to spectral profile 166 from the same sample arranged as a point source, as indicated by comparing the full width at half maximum (FWHM) for each profile, indicated at 169 and 170, respectively.

The spectral profile and two-dimensional spectral image detected from a well can be produced by convolving the well image size and/or shape with the spectrum that would be produced from a point or line source in place of the well. Accordingly, each point arranged along a line parallel to the spectral axis in a spectral image of the well does not correspond to a single wavelength from the sample, but to a range of wavelengths determined by the sample/well size and/or shape (and the system optics). In some examples, calibration of the spectral imaging system thus can measure, at least in part, how each well alters and/or broadens spectral images and/or profiles measured from the well relative to a point/line source.

FIG. 2B shows selected portions of another exemplary spectral imaging system 180. System 180 can have an optical system 182 with a diffraction grating 184 that disperses light from a two-dimensional array of examination sites 186 to form a series of corresponding arrays of different diffraction orders, e.g., arrays 188-194 of spectra 196. (Additional arrays (e.g., −3, +3, −4, +4, etc.) can be formed and detected but are not shown here to simplify the presentation.) Arrays 188-194 can flank a zero order array 198 of nonspectral images produced by nondispersed light from the examination sites passing through the grating without being diffracted.

The distance between the arrays can be adjusted according to the line spacing of the grating, as specified by the grating equation. Accordingly, the grating can be selected to provide an array of spectra of the same order in which the array is collectively resolved from adjacent arrays, using light of a selected wavelength range. For example, the grating can be selected such that the array of +1 (or −1) diffraction order spectra is collectively resolved from nondispersed (zero order) light and/or from 2 (or −2) diffraction order spectra. Accordingly, a detector 200 of the imaging system can be positioned such that each spectrum 196 of one of the diffraction orders (+1 here) falls on the detector concurrently. In some examples, the detector can be positioned also to detect one or more adjacent spectra, such as one or more zero order images, indicated by a dashed extension of the detector at 202, to serve as a fiducial(s) to correct for variability in sample positioning and/or optical system alignment (e.g., see Example 8). A higher order array (such as +2 or −2) can be detected instead (or in addition). However, the signal intensity generally decreases for higher order arrays relative to lower order arrays.

FIG. 3 shows selected portions of a series of spectral imaging systems having various exemplary optical systems with distinct arrangements of optical relay structures, particularly spectral filters.

Imaging system 220 can include an optical system 222 with a grating 224 that disperses light received from an array of examination sites 226. The light can, for example, be visible light of about 400 nm to 800 nm and/or light of a wavelength range determined by selection of a suitable luminophore(s) and/or light source. The optical system also can direct the dispersed light to a detector 228 as a corresponding array 230 of spectra 232 disposed in an overlapping arrangement on the detector. In particular, adjacent ends of the spectra, indicated at 234, can overlap (generally the longer wavelength end of one spectrum overlapping the shorter wavelength end of an adjacent spectrum along a dispersion axis). An overlapping arrangement, as used herein, is any arrangement in which there is significant interference or crosstalk between adjacent spectra such that analysis of the spectra is impaired.

Imaging system 220 can be modified to form an imaging system 240 with an optical system 242 including a short-pass filter 244. The short-pass filter can selectively restrict passage of light of longer wavelengths, to truncate each spectrum at one end, indicated at 246. The short-pass filter can be sufficient to effectively remove the crosstalk between adjacent spectra. Alternatively, sufficient overlap and crosstalk can still be present, indicated at 248.

Imaging system 220 alternatively can be modified to form an imaging system 260 with an optical system 262 including a long-pass filter 264. The long-pass filter can selectively restrict passage of light of shorter wavelengths, to truncate each spectrum at the other end, indicated at 266. The long-pass filter can be sufficient to effectively remove the crosstalk between adjacent spectra. Alternatively, sufficient overlap and crosstalk can still be present, indicated at 268. The system can have only one long-pass filter or can include at least a first long-pass filter (such as a beam splitter) that selectively removes excitation light from emitted light and a second long-pass filter following the first long-pass filter in the optical path and configured substantially exclusively to receive emitted light (relative to excitation light) and to truncate the spectrum of the emitted light.

Imaging system 220 alternatively can be modified to form an imaging system 280 with an optical system 282 including both short-pass filter 244 and long-pass filter 264. The filters in combination can truncate each spectrum at opposing ends to substantially reduce crosstalk between the spectra, indicated at 284.

The filters can be disposed at any position(s) in the optical system, preferably in a collimated beam zone of the optical path (such as after the objective lens or before the detector lens in the optical path). For example, each filter can be disposed before (upstream of) or after (downstream of) the dispersion element in the optical path for emitted light. Furthermore, the filters can be separate components or can be combined in a single component as a relatively broad spectrum band-pass filter. The filters can select any suitable range of wavelengths. In exemplary embodiments, the long-pass filter can selectively permit passage of light having wavelengths of longer than about 450 nm to about 550 nm, or of longer than about 500 nm; the short-pass filter can selectively permit passage of light having wavelengths of shorter than about 550 to about 700 nm, or of shorter than about 600 to about 650 nm; and both filters, if present together, can selectively permit passage of about a 50-200 nm or about a 100-150 nm range of wavelengths and/or can restrict passage of light having wavelengths of less than about 500 nm and greater than about 650 nm.

The spectral imaging system can be of any suitable size and weight and can be used in any suitable environment. For example, the system can have a size and weight (e.g., greater than about 5,000 cc and/or greater than about 10 kg) that restricts ready transport of the system, such that the system can be relatively permanent once installed. Alternatively, the system can have a size and weight (e.g., less than about 5,000 cc and/or less than about 10 kg) that facilitates portability, and/or a size and weight (e.g., less than about 1000 cubic centimeters and/or less than about 2 kg) that permits the system to be hand-held. Accordingly, the system can be used in medical applications, (e.g., for biodefense, forensics, paternity conflicts, clinical diagnosis, and/or the like) as a portable and/or hand-held medical device that can be transported readily to various testing sites.

II. ILLUMINATION SYSTEMS

An illumination system, as used herein, generally comprises any mechanism for producing light capable of illuminating, and/or inducing a suitable or desired response from, a sample. For example, when used in an optical assay, light from the illumination system can, as a result of illuminating a sample, produce emitted (e.g., photoluminescence) light (using an excitation light source), transmitted light, reflected light, and/or scattered light, among others. These different forms of light can be present exclusively, or in various combinations, and can include ultraviolet, visible, and/or infrared light, among others.

The illumination system can have one or more light sources. Each light source can include continuous wave and pulsed lasers, arc (e.g., xenon) lamps, incandescent (e.g., tungsten halogen) lamps, fluorescent lamps, electroluminescent devices, laser diodes, and/or light-emitting diodes (LEDs), among others. Such light sources can be capable of use in one or more illumination modes, including continuous and/or time-varying (e.g., pulsed or sinusoidally varying) modes, among others, depending on system configuration and/or intended application. For example, an arc lamp or continuous wave laser can be used to provide continuous illumination, and a pulsed laser or pulsed LED can be used to provide intermittent illumination. Such light sources also can produce coherent, incoherent, monochromatic, polychromatic, polarized, and/or unpolarized light, among others. For example, an arc lamp can be used to provide (at least initially) incoherent, polychromatic, unpolarized light, and a laser can be used to provide (at least initially) coherent, monochromatic, polarized light, among other possibilities.

The light source can be selected, at least in part, based on the spectrum of light produced. Generally, the light source can produce light (e.g., ultraviolet and/or visible light) capable of exciting the samples (and particularly luminophores therein) for light emission. Accordingly, the light source(s) can be selected according to its ability to produce light of a wavelength, wavelength range, and/or set of wavelength ranges that is absorbed by and excites one or more luminophores in the samples. In some examples, the light source(s) can be selected for its ability to excite every luminophore of a set or two or more luminophores disposed in the samples, such that each luminophore detectably emits light.

The light source(s) can be disposed in any suitable position relative to the sample holder and emission optics. For example, the light source can be disposed on the same side of the sample holder as the emission optics or can oppose the emission optics across the sample holder. If disposed on the same side as the emission optics, the light source can be disposed substantially on-axis (i.e., near or on an optical axis defined by the emission optics) or can be disposed substantially off-axis. An on-axis light source can be achieved, for example, by disposing a plurality of light sources around the optical axis, oriented to direct excitation light toward the sample holder. An off-axis light source can be achieved, for example, via an optical element(s), that bends a beam(s) from the light source to bring the beam coincident with the optical axis.

The illumination system can include a light source(s) used in combination with various source optics (such as any combination of the optical elements described below in Section IV). The source optics can be used to alter the nature of the light output by the light source (e.g., its color (spectrum or chromaticity, such as via filtering), intensity, polarization, and/or coherence, among others). Alternatively, or in addition, the source optics can be used to direct and/or alter the size, shape, and/or numerosity of the light beam(s) (e.g., to illuminate selected locations in an examination area with one or more light beams). Furthermore, the source optics can include a light homogenizer(s)/mixer(s) to increase the uniformity of illumination of the examination area. Alternatively, or in addition, the source optics can include a collection optical element(s) to increase the percentage of light from the light source that is directed to the examination area. In some examples, the collection optical element can be a light guide that operates by total internal reflection. The light that is ultimately incident on the sample(s) can be produced by one or more light sources, and can be directed and/or modified, optionally, by one or more optical elements operatively disposed between the light source(s) and the examination area. The resultant light beam or beams can be one or more of various forms, including but not limited to diverging, collimated, and converging, among others.

The illumination system can be configured to illuminate an array of samples in an examination area concurrently or at different times. If illuminated at different times, the samples can be serially illuminated one by one, line by line (e.g., one row or one column at a time), and/or section by section (e.g., two or more rows or columns at once), and/or the like. Furthermore, if illuminated at different times, subsets of a sample array can be illuminated with distinct light sources (e.g., operated serially), and/or the same light source directed serially onto the subsets, among others.

In some examples, the illumination system can have at least two light sources (and/or illumination assemblies) that illuminate samples with distinct wavelengths of light. For example, the light sources can include a light source that produces light of shorter wavelengths, such as a blue LED, and a light source that produces light of longer wavelengths, such as green LED. The at least two light sources or assemblies can be selected, for example, to excite different dyes in the samples, based on different absorption spectra of the different dyes. The light sources or assemblies can be turned on at the same time or can be turned on serially. In some embodiments, excitation light of the longer-wavelength source can be removed from the emission optical path via a notch filter in the emission optics.

Further aspects of illumination systems that can be suitable for spectral imaging systems of the present teachings are described elsewhere in the present teachings, such as Example 5, and in the patent applications listed above under Cross-References, which are incorporated herein by reference.

III. EXAMINATION AREAS AND SAMPLE HOLDERS

The imaging systems of the present teachings can include an examination area operatively disposed in relation to the optical system. In particular, the examination area can be positioned such that the examination area is illuminated effectively by the illumination system and imaged effectively by the detector for emitted light dispersed by the emission optics. The examination area (defining an object plane) can be defined adjacent or on a receiver structure, such as a platform or stage. The receiver structure can be configured to receive (and optionally retain) a sample holder and position the sample holder such that samples of the sample holder are disposed in the examination area, particularly in a two-dimensional array of examination sites of the examination area. The examination sites can be defined substantially by the positions in which the samples are disposed in the examination area. Alternatively, or in addition, the examination sites can be predefined in correspondence with regions of interest of a detector of an imaging system, such as by calibration.

A sample holder (a sample-support device), as used herein, generally comprises any mechanism for supporting one or more samples in examination sites of an examination area. In typical embodiments, the sample holder allows for the receipt and/or transmission of light relative to one or more samples supported by the device. General examples of suitable sample holders can include trays, wells, tubes, containers, channels, chambers, frames, carriages, holders, slides, shelves, stages, housings, and/or the like. Specific examples of suitable sample holders can include microplates, PCR plates or cards, cell culture plates, biochips, hybridization chambers, chromatography plates or columns, and/or microscope slides, among others.

The sample holders can be configured to allow top detection (e.g., by having an open or at least partially transparent top), bottom detection (e.g., by having an at least partially transparent bottom), and/or side detection (e.g., by having an at least partially transparent side), among others.

Each sample holder can provide a two-dimensional array of locations or compartments for supporting samples. The array can have any suitable arrangement of the locations/compartments, including rectilinear (with a plurality of rows and columns), circular, irregular, and/or the like. (In some examples, a ring-light illuminator can be suitable for illumination of a circular arrangement of wells.) Specific locations in the sample holder, such as wells in microplates, PCR plates/cards, and cell culture plates, and array sites on biochips, can comprise assay sites. For example, microplates (and/or PCR plates/cards, microtiter plates, and/or cell culture plates) can include arrays of 6, 12, 24, 48, 96, 384, 864, 1536, 3456, and/or 9600 such assay sites, among others.

The sample holders and/or arrays suitable for spectral imaging systems can have standard or nonstandard features. Assay sites (e.g., wells) can be arrayed with a uniform spacing or a nonuniform spacing. For example, all rows and all columns of the wells can be aligned or a subset of the rows and/or columns can be offset from the others (such as in a staggered arrangement). In some embodiments, the spacing between adjacent rows relative to the spacing between adjacent columns can be different. For example, the spacing between assay sites along a sample holder axis corresponding to a spectral axis of the system can be greater than their spacing orthogonal to this sample holder axis. This arrangement can provide more efficient use of the detector. For example, excess lateral spacing (corresponding, generally, to wasted detector area) between laterally adjacent spectral images can be minimized while providing a sufficient longitudinal dimension for dispersion of spectral components of each spectral image.

The assay sites of a sample holder can have any suitable shape and size. The sites can be two-dimensional, such as areas on a surface (generally disposed in fluid communication), or can be three-dimensional, such as wells (generally disposed in fluid isolation). In any case, each site can have any suitable shape in a plane defined by the sample holder, such as circular, polygonal (e.g., rectangular), elliptical, oval, and/or the like. In some examples, each site can be elongate in the plane of the sample holder. Elongate sites can provide a more line-like emission of light from the sites. The elongate sites thus can be oriented with the long axis of each site orthogonal to a sample holder axis corresponding to a spectral axis of dispersion. This orientation can provide more line-like spectral components and thus better resolution (less overlap and/or greater spacing) between spectral components within each spectral image. If three-dimensional, each site can be a well having any suitable three-dimensional shape, such as cylindrical, semi-spherical, conical, frustoconical, and/or polyhedral, among others. Furthermore, each well can have any suitable depth relative to the well's area. Relatively deeper wells can be suitable, for example, to increase the volume of sample that can be held by each well and/or to reduce the angle of light emission from samples disposed in the wells (e.g., with samples occupying only a lower portion of the wells). Relatively shallower wells can be suitable, for example, to increase the angle of light emission from samples disposed in the wells. Overall, the wells can provide compartments of any suitable size and volume. For example the wells can be about 0.1 to 10 mm or about 0.5 to 5 mm in diameter and/or can have a volume of at least about 0.1 µL, about 0.1 to 10 µL, or about 0.5 to 5 µL, among others.

The sample holder can be covered and/or sealed hermetically with a sealing element to restrict evaporation of fluid from samples disposed in the assay sites, particularly if the samples are heated. For example, the sample holder can be covered/sealed with a cover for the entire array, and/or individual assay sites (or sets of assay sites) can be covered/sealed individually or in sets with caps or plugs.

Further aspects of sample holders are described elsewhere in the present teachings, such as in Example 6, and in the patent applications listed above under Cross-References, which are incorporated herein by reference.

IV. OPTICAL SYSTEMS

Optical systems, including input (illumination) and/or output (emission) relay structures, as described herein, generally comprise any mechanism(s) for directing, transmitting, and/or conducting light within the imaging systems such as from a light source toward a sample (or examination area) and/or from a sample (or examination area) toward a detector. The optical system can include optical relay structures that stand alone and/or that are integral to other system components, such as the light source and/or detector, among others. Each optical relay structure can be configured to direct one or more light beams, in the same or different directions, along the same, multiple, or different optical paths.

A. Overview of Optical Relay Structures

Each optical relay structure can include any suitable combination of one or more optical elements. These elements independently can be part of a single (e.g., excitation or emission) relay structure, or can be shared between two or more relay structures. Exemplary optical elements can include (1) reflective elements, such as concave, planar, and/or convex mirrors, among others, (2) refractive elements, such as converging, diverging, concave, convex, and/or planoconvex lenses, including circular and/or cylindrical lenses, among others, (3) transmissive or conductive elements, such as glass or quartz fiber optics and/or liquid light guides, (4) diffractive elements such as gratings or other dispersion elements, and/or (5) subtractive elements (such as filters), among others.

The optical relay structure(s) can be selected, in conjunction with the light source(s) and/or detector(s), to allow any suitable or desired combinations of illumination and/or detection. For example, these components can be arranged to allow same-side, (locally) anti-parallel or straight-on ("epi") illumination and detection, such as top illumination and top detection, or bottom illumination and bottom detection, respectively. Alternatively, or in addition, these components can be arranged to allow opposite side, (locally) parallel or straight-through ("trans") illumination and detection, such as top illumination and bottom detection, or bottom illumination and top detection, respectively. Alternatively, or in addition, these components can be arranged to allow illumination and/or detection at oblique angles. For example, illumination light can impinge on the bottom of a sample holder at an acute angle (e.g., about 45 degrees) relative to detection. Such oblique illumination and detection can reduce the amount of excitation light reaching the detector, relative to straight-on epi systems (light source and detector directed at about 90 degrees to sample holder) or straight-through trans systems (light source directed through a sample holder directly at a detector). Epi systems are especially suitable for photoluminescence assays, trans systems are especially suitable for absorbance assays, and oblique systems (with the incidence angle set above the critical angle) are especially suitable for total internal reflection assays, among others.

B. Dispersion Elements

An optical dispersion element (a color separator), as used herein, generally comprises any mechanism for dispersing light spatially according to its wavelength composition.

The dispersion element can use any suitable mechanism(s) and/or component(s) for dispersing light. Exemplary mechanisms can include diffraction, interference, and/or refraction, among others. Exemplary components can include (diffraction) gratings, interferometers, and/or prisms, among others. In some embodiments, the dispersion element can include two or more sequentially acting components, employing the same or different mechanisms, with the first component achieving a coarse color separation, and the second component achieving a finer or final color separation.

Gratings can have any suitable structure. The gratings can be transmission gratings and/or reflection gratings, among others. Furthermore, the gratings can have a planar or nonplanar surface at which light is received. Exemplary nonplanar surfaces can include parabolic, toroidal, and/or spherical surfaces, among others. The gratings can have any suitable spacing of lines (generally, grooves to provide ruled gratings) and/or fringes (holographic gratings), according to the application. A suitable spacing of lines and/or fringes can be determined theoretically (e.g., by using a diffraction grating equation and/or empirically for a particular system configuration). Generally, the spacing can be decreased (e.g., the number of lines/mm increased) to increase the amount of spectral dispersion (e.g., to lengthen each spectral image on the detector and/or to increase the spacing between adjacent spectra of the same or different diffraction orders) or the spacing can be increased for the opposite effect. In some examples, the grating can be a blazed grating, that is, a grating optimized for a particular wavelength (or spectral region) and/or a particular angle of incidence (or range of angular incidences).

The dispersion element can separate multi-wavelength light by directing light with different wavelengths along different paths (e.g., in different directions, at different angles, etc.) The separation can be partial or complete, and can create bands or beamlets of light, which can be continuous or discrete, and which can be partially overlapping or completely distinct. The character of the separation typically will be determined at least in part by the character of the light being separated. Thus, input light with several well-spaced wavelength components can give rise to separated output light at several discrete (well-spaced) positions, while input light with closely or continuously spaced wavelength components can give rise to separated output light over a continuous set of positions. The character of the separation also can be determined at least in part by the shape of the sample (e.g., as determined at least in part by the volume and/or area of the sample and the shape of the well supporting the sample). For example, a sample having a shape that deviates from a point or line source can tend to produce a corresponding deviation from a point or line in the shape of the dispersed spectral components (e.g., excitation of a sample in a circular well can produce circular (or oval) spectral components in a spectral image of the sample). More generally, any deviation from a point or line source can produce a spectrum in which the entire spectrum and spectral components thereof are broadened to reduce the resolution between adjacent spectra and/or between spectral components within the spectrum.

An imaging system with a particular well size/shape can provide any suitable degree of broadening of a corresponding spectrum relative to a spectrum of the same spectral composition produced by a point source in place of a well. The broadening can be by a distance on the detector corresponding to a spectral distance of at least about 10 nm or 20 nm, among others, as measured for the width of a peak within the spectrum at half maximum (FHWM) or at 10% of maximum intensity. For example, an exemplary peak having a width measured at half maximum intensity (FWHM) of 30 nm can be broadened to at least about 40 nm or 50 nm. Accordingly, absolute wavelengths can be difficult to measure with the spectral imaging system because light of a single wavelength from the sample may not fall as a sharp line or point on the detector but can be spread out in opposing directions parallel to the spectral axis according to the sample size and shape.

The separated light generally can form any distinguishable pattern. Thus, the separated light can form a linear array, in which the average wavelength of light varies with position along the linear array.

The separated light can be directed onto a common detector, onto separate detectors, or onto a combination of detectors. The relationship between wavelength and position on the detector(s) can be determined empirically, for example, using input or calibration light of known wavelength(s). Alternatively, or in addition, the relationship between wavelength and position on the detector(s) can be determined theoretically, for example, by calculating the optical paths for light of different wavelengths. The position(s) of light on the detector can be determined by a variety of factors, including (1) the mechanism used to separate the light, (2) the angles at which the light enters and leaves the dispersion element, (3) the wavelength(s) of the light, (4) the distance between the dispersion element and the detector(s) (generally, greater distances between the dispersion element and detector(s) will give rise to greater separations between light of different wavelengths on the detector(s)), (5) the magnification (or optical reduction/demagnification) of the system, (6) the focal length of the detector lens, and/or (7) the type of pattern (e.g., linear versus circular) formed by the separated light, among others.

The spatial distribution or pattern of detected light can be converted into information about the amount (including presence/absence), distribution, identity(ies), structure, and/or the like of components of the sample, using any suitable method. These methods can include simply looking up a result in a look-up table (e.g., position (x,y) on the detector corresponds to light of wavelength λ (or wavelengths within some extended range (e.g., $\lambda_1$ to $\lambda_2$)) emitted from position (X,Y) (or positions within some extended range) in the sample holder, evaluating a function expressing the relationship between these parameters, and/or the like. The desired result can be obtainable simply by noting qualitatively the presence or absence of light at a particular position on the detector (subject, in some cases, to some threshold amount), or it can be obtainable by determining quantitatively the amount of light (intensity, number of photons, amount of energy, etc.) detected at the position, among others.

The dispersion element can be disposed, in some embodiments, so that it acts only on light directed from a sample toward a detector, without acting on (or, in most cases, even contacting) light directed from a light source toward a sample.

C. Miscellaneous Optical Elements

The spectral imaging system, and/or components thereof, also can include miscellaneous optical elements capable of performing additional and/or duplicative optical functions. These optical elements can include (1) intensity filters (such as neutral density filters) for reducing the intensity of light, (2) spectral filters (such as interference filters, diffraction gratings, a colored material such as colored glass, and/or prisms) for altering or selecting the wavelength(s) of light (e.g., for separating longer-wavelength emission light from shorter-wavelength excitation light, in single-photon photoluminescence, for defining the maximum wavelength of emitted light that reaches the detector, and/or for separating shorter-wavelength emission light from longer-wavelength excitation light, in multi-photon photoluminescence), (3) polarization filters (such as "polarizers") for altering or selecting the polarization of light, (4) "confocal optics elements" (such as an aperture or slit positioned in an intermediate image plane) for reducing or eliminating out-of-focus light, (5) beam collimators for converting input light (particularly diverging input light) into an at least substantially collimated light beam, (6) beam expanders for increasing the cross-sectional area of a beam of light, (7) beam homogenizers (such as a fiber optic cable or liquid light guide) for enhancing the spatial uniformity of light, and/or (8) reference monitors for correcting for variations (e.g., fluctuations and/or inhomogeneities) in light produced by a light source and/or other optical elements. These elements can be functional in one or more of the space, time, and/or frequency domains, as necessary or desired.

A spectral filter element generally acts to reduce or eliminate emission at selected wavelengths and/or over selected ranges of wavelengths (i.e., to reduce or remove undesired spectral components). These functions can be accomplished via any suitable mechanism, using a single subtractive element or a combination of subtractive elements. Suitable subtractive elements include filter elements such as (1) short-pass (cut-off) filters, which selectively pass short-wavelength light and reject long-wavelength light, (2) long-pass (cut-on) filters, which selectively pass long-wavelength light and reject short-wavelength light, (3) band-pass filters, which selectively pass light with a particular wavelength (or range of wavelengths) and reject light with lower and higher wavelengths, and/or (4) band-reject (or notch) filters, which reject light with a particular wavelength (or range of wavelengths) and pass light with shorter and longer wavelengths, among others. Short-pass and long-pass filters (also know as edge filters) can be characterized by a cut-on or cut-off wavelength, among others, and band-pass and band-reject filters can be characterized by a center wavelength and a bandwidth, among others. Suitable subtractive elements can include thin-film (e.g., metallic and/or interference) coatings, colored filter glass, holographic filters, liquid-crystal tunable filters, and/or acousto-optical tunable filters, among others. These subtractive elements can work by absorbing, reflecting, and/or bending (refracting or diffracting) light, among others. In some embodiments, the subtractive element can work by filtering portions or all of the excitation light, either before or after the excitation light illuminates samples. Filtering portions before sample illumination can be performed, for example, on portions which, when absorbed, give rise to undesired spectral components of the emission.

The relative positions of any intensity, spectral, polarization, and/or other optical elements generally can be varied without affecting the operation of the spectral imaging system. In addition, if there is more than one optical path, for example, to permit top and bottom or oblique illumination and/or detection, optical elements can be shared and/or used independently in each path. The particular order, positions, and combinations of optical elements for a particular experiment can depend on the apparatus, the assay mode, and the sample (target material), among other factors. In some cases, optical elements can be associated with an exchange mechanism, such as a wheel or slider, that allows convenient and automatable placement and exchange of optical elements by rotating, sliding, or otherwise bringing preselected optical elements into or out of the optical path. In some examples, optical elements can be associated with an adjustment mechanism (automated or manual), for example, to adjust the axial position and/or alignment of optical elements, and/or to increase or decrease magnification (or optical reduction) of images, among others.

V. DETECTORS

A detector, as used herein, generally comprises any mechanism for detecting light transmitted or otherwise originating from a sample and optionally converting the detected light into a representative signal.

Exemplary detectors can include film, charge-coupled devices (CCDs), complementary metal oxide semiconductor (CMOS) devices, intensified charge-coupled devices (IC-CDs), charge injection device (CID) arrays, vidicon tubes, photomultiplier tubes (PMTs), photomultiplier tube (PMT) arrays, position sensitive photomultiplier tubes, photodiodes (such as photodiode arrays), and/or avalanche photodiodes, among others. Such detectors can be capable of use in one or more detection modes, including (1) imaging and point-reading modes, (2) discrete (e.g., photon-counting) and analog (e.g., current-integration) modes, and/or (3) steady-state and time-resolved modes, among others. The detectors can be configured to receive a two-dimensional array of light, which can be separated parallel to a first dimension according to position in a sample or sample array, and parallel to a second dimension according to position and spectral composition. Toward this end, the detector can include bins (e.g., regions of interest and/or sub-regions with the regions of interest) for detecting light from different samples and/or of different colors from the samples, for example, corresponding substantially to light from different luminophores. These bins can be the same or different sizes, and can be formed of one or a plurality of sub-bins, or pixels (sensor elements), depending in part on the average separation between spectral peaks outputted by the color separator.

The detector can be used alone or in combination with various optics and/or other mechanisms (such as the optical relay structures described above). These optics and/or other mechanisms can be used to alter properties of the light (e.g., color, intensity, polarization, coherence, and/or size, shape, and/or numerosity of the light beam(s), as described elsewhere herein), prior to its detection. In some embodiments, the detector can be part of or coupled to a spectrograph or spectroscope for analyzing the spectral composition of the detected light.

VI. CONTROLLERS

A controller, as used herein, generally comprises any mechanism for controlling components and/or other aspects of a spectral imaging system. These components and/or other aspects can include the light source(s), optical relay structures, registration device, fluidics mechanism, thermal control device, detector, and/or data analysis, among others. For example, the controller can determine and/or change (1) the wavelength, intensity, and/or (spatial and/or temporal) uniformity, and/or spatial position/direction of light produced by the light source; (2) the order and timing of sample delivery by the registration device and image acquisition by the detector; (3) the wavelength and/or intensity of light detected by the detector; (4) the temperature of samples disposed in or near the examination area; (5) the relative timing of temperature regulation, light source actuation, and detector exposure/detector actuation; and/or (6) the composition of samples in or near the examination area, among others. The controller can include hardware, software, firmware, and/or a combination thereof, and can be any device, or combination of devices, adapted to store and execute instructions to control associated imaging system components. The controller can include one or more of various devices, such as a computer, computer server, microprocessor, memory, logic unit, and/or processor-based system capable of performing a sequence of logic and/or arithmetic operations. In addition, processing can be centralized (with two or more components sharing a common controller) and/or distributed (with one or more components having their own dedicated controllers, acting alone, or connected to one another and/or a central controller).

The controller also or alternatively can be configured to process sample/image information detected by the detector. For example, the controller can (1) identify image regions corresponding to individual samples and/or individual sample spectral components, and/or (2) relate the information detected by various regions/pixels/bins of the detector to particular samples, spectral components, and/or assays, among others.

VII. THERMAL CONTROL SYSTEMS

A thermal control system, as used herein, generally comprises any system for regulating the temperature of samples. The thermal control system can be configured to add heat to samples (e.g., including a heater(s)) and/or to remove heat from samples (e.g., including a cooler(s)). The thermal control system also can include a temperature sensor configured to measure temperature adjacent (or in) the samples. The thermal control system further can include or be coupled to a controller that uses the measured temperature to determine when, how long, where, and/or at what level, among others, to actuate the heater and/or cooler, to achieve and maintain a suitable target temperature or suitable profile of target temperatures for the samples.

The heater (or heaters) and/or cooler (or coolers) can operate by any suitable mechanism and can have any suitable structure. Exemplary mechanisms for heating and/or cooling can be by conduction (i.e., by contact), convection (i.e., through air), and/or radiation (i.e., via waves and/or particles). Exemplary heaters/coolers can include resistive elements, Peltier devices (e.g., solid state devices that operate by a thermoelectric effect using a thermocouple(s)), infrared lamps, refrigeration units (e.g., by gas expansion/compression), fluid circulators (e.g., fans or fluid conduits), and/or the like.

The temperature sensor (or sensors) can have any suitable structure and can be a contact or noncontact device. Exemplary temperature sensors can include thermocouples, thermistors, resistance temperature devices, radiation thermometers (pyrometers), thermal imagers, (liquid in glass) thermometers, and/or the like.

The thermal control system can be disposed in any suitable position relative to the sample holder/samples. For example, the thermal control device can be disposed below, above, laterally (i.e., adjacent one or more sides), and/or substantially enclosing the sample holder (e.g., to provide a heating/cooling chamber). In exemplary embodiments, the thermal control system is disposed below the sample holder and includes a conductive member that contacts the bottom of the sample holder to provide conductive heating/cooling.

The thermal control system can be controlled to provide any suitable temperature profile for the samples, and the profile can be the same or different for each sample of a sample holder. For example, the thermal control system can be configured to rapidly heat or cool samples. Exemplary rates of rapid heating and/or cooling include a rate of temperature change of at least about 10° C. per minute, or at least about 1, 2, 5, or 10° C. per second. In some embodiments, the thermal control system can maintain the temperature of the samples at a constant temperature (e.g., below, around, and/or above room temperature). In some embodiments, the thermal control device can change the temperature of the samples during an analysis (e.g., to test the effect of different temperature on the samples and/or to promote chemical reactions (e.g., enzyme-catalyzed reactions) and/or binding reactions (such as binding or unbinding) in the samples, among others).

VIII. CALIBRATION OF SPECTRAL IMAGING SYSTEMS AND SAMPLE ANALYSIS

The spectral imaging systems of the present teachings can be calibrated and used for analysis of test samples at any suitable relative times and in any suitable fashion. For example, the imaging systems can be calibrated before, during, and/or after sample analysis, as described further below.

A spectral imaging system can be calibrated by any suitable approach at any suitable time(s) during and/or after the manufacture of the system. Accordingly, calibration can be performed before an imaging system is sold to a customer and/or can be performed at the site(s) of operation by a user (including service personnel). On-site calibration can be performed to calibrate the system for the first time or as a re-calibration of the system to adjust for changes in the system configuration. On-site calibration can be particularly suitable for a portable system, which can be subject to more frequent mechanical shocks, which can alter the alignment of system components.

Figure 4:
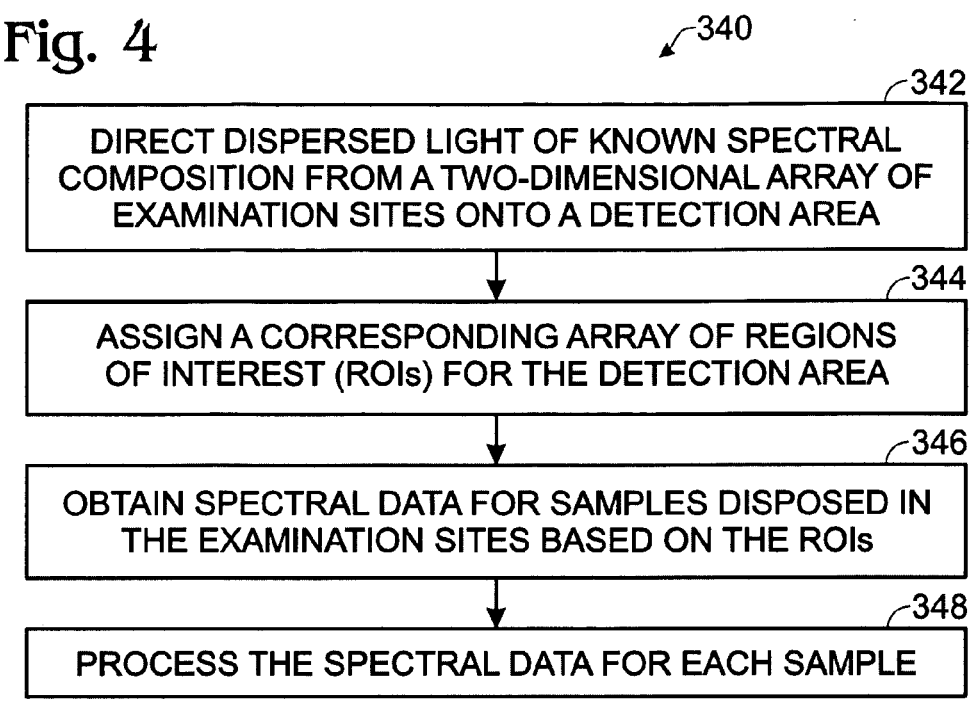
FIG. 4 is a flowchart listing steps that can be performed with a spectral imaging system in an exemplary method of sample analysis that includes calibration, in accordance with aspects of the present teachings.

FIG. 4 shows an exemplary flowchart 340 listing steps that can be performed in a method of sample analysis that includes calibration (e.g., the first two steps listed in the flowchart). The steps can be performed in any suitable order, in any suitable combination, and any suitable number of times. Furthermore, the steps can be combined in any suitable way with other steps described elsewhere in the present teachings to perform other methods of sample analysis.

Dispersed light of known spectral composition can be directed from one or more sites of a two-dimensional array of examination sites onto a detection area, shown at 342. Known spectral composition, as used herein, means that the light has at least one spectral feature of known wavelength (such as an intensity peak or valley, among others), or that at least substantially every spectral feature of the light is known. The light can be emitted from a standard source and/or a test sample to be assayed. The standard source or test sample can include one or more luminophores (e.g., fluorescent dyes (fluorophores)). Alternatively, the light can be excitation light (e.g., from a light source(s) of the illumination system) that is filtered or unfiltered. The light of known spectral composition can be directed concurrently to the detection area (e.g., for calibration with only one dye, only a dye mixture, or only one configuration of excitation light). In other examples, different spectral components or combinations of spectral components can be directed to the detection area at different times (e.g., to perform calibration using two or more dyes placed serially into the examination area of the imaging system).

A corresponding array of regions of interest can be assigned for the detection area, shown at 344. The array of regions can be assigned relative to the detection area based on detection of dispersed light of known spectral composition from any suitable number of examination sites, including only one, at least a pair, a two-dimensional arrangement, at least most, or all of the examination sites. Accordingly, each region of interest can be assigned based on detection of light of known spectral composition from a corresponding examination site. Alternatively, a subset of the regions of interest can be assigned without detecting light of known spectral composition from corresponding examination sites. For example, if dyes are used for calibration, the dyes may not be placed in every well of a sample holder disposed in the examination area (and/or can be in wells that are ignored for calibration to simplify data processing). In this case, the array of regions can be generated, at least in part, by interpolation, extrapolation, and/or by positioning a predefined array of regions in relation to the detection area based on signals detected from one or more sentinel examination sites.

Spectral data can be obtained for samples disposed in the examination sites based on the regions of interest, shown at 346. The samples can be the same test samples used for calibration or can be test samples disposed in examination sites after calibration standards are removed from the examination sites. Using test samples for calibration can be suitable if the test samples provide a known spectral composition at the outset of a reaction, such as in a kinetic reaction that monitors changes in spectral data from samples over time. The spectral data can be obtained in exact correspondence with the assigned regions of interest, for example, selecting a portion of the detected data defined by a region of interest and/or selectively detecting spectral data for each sample using a corresponding region of interest of the detector. Alternatively, the positions the regions of the interest can be adjusted before the spectral data is obtained for individual samples. For example, the regions of interest can be moved translationally and/or pivotally based on detection of a fiducial(s) (see Example 8) and then appropriate portions of the detected data can be selected and/or the new (adjusted) regions of interest used to selectively detect spectral data for individual samples.

The spectral data can be processed for each sample, shown at 348. Processing can include simplifying the spectral data, such as summing the spectral data orthogonal to the dispersion axis, to create a one-dimensional vector from two-dimensional data. Alternatively, or in addition, processing can include binning portions of the spectral data for a sample. A part or all of the spectral data for a sample (and/or for a region of interest) can be placed into uniform bins (such as bins that are two, three, four, five, etc.) pixels wide (in a dimension parallel to the spectral axis) and processed as part of the bin (e.g., summed). Alternatively, or in addition, a part of all of the spectral data for a sample (and/or for a region of interest) can be placed into nonuniform bins, such as bins centered around intensity peaks in the spectral data, and processed as part of the bin (e.g., summed). For example, each expected intensity maxima in the spectral data for a sample or detector region can have its own bin(s). In addition, processing can include removing background. Processing also can include determining the amount (including presence/absence) of a luminophore signal for each sample. Moreover, processing can include correlating the amount determined with a sample aspect, to provide information about the sample. Furthermore, processing can include detecting a change, if any, in spectral data for a sample over time, to provide kinetic data for a reaction or interaction occurring (or not occurring) in the sample. The change can be related to time and/or to cycle number in repetitive thermal cycling, among others.

Figure 5:
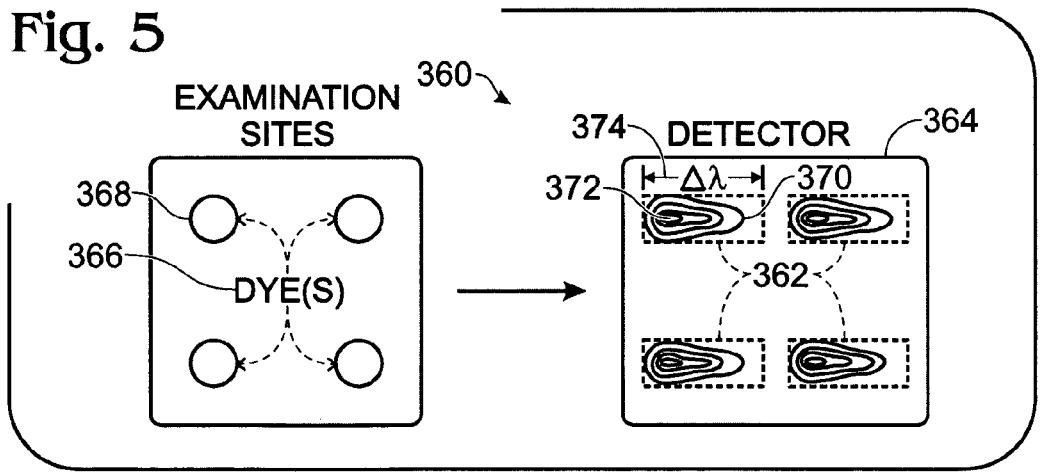
FIG. 5 is a schematic view of selected portions of an exemplary spectral imaging system illustrating assignment of regions of interest on a detector using spectra from a luminophore(s) disposed in each examination site.

FIG. 5 shows selected portions of an exemplary spectral imaging system 360 illustrating assignment of regions of interest 362 on a detector 364. One or more luminophores ("dyes") 366 can be disposed in each examination site 368. In some examples, the same set of one or more luminophores can be disposed in one or more, most, or all of the examination sites, such as by disposing the luminophores via a sample holder having wells in which the luminophores are contained. In some examples, the same set of luminophores is disposed in most or all of the examination sites, optionally in substantially the same relative amounts and/or in known amounts. If a set of luminophores is disposed in the examination sites, the luminophores can be disposed individually (e.g., serially) and/or as one or more mixtures of two or more or all of the luminophores of the set. The luminophores can be the same luminophores to be used for assays with distinct test samples or can include at least one or more (or be all) luminophores that are distinct from those used in test samples.

Each region of interest 362 can be assigned based on a spectrum 370 (or spectra) produced by the luminophore. For example, here, spectrum 370 can allow assignment of an associated region of interest 362 according to a detected intensity maximum 372, minimum, threshold, transition, and/or the like. Furthermore, the region of interest can be assigned at least in part based on a predefined size of the region of interest. The predefined size can be based, at least in part, on a predefined or measured pixel to wavelength relationship on the detector along a spectral axis. For example, in exemplary embodiments, light can be dispersed at about 1 nm of wavelength per pixel on the detector. Accordingly, an approximate wavelength range 374 (ignoring spectral broadening due to the sample size/shape) can be selected based on the pixel length of the region of interest. For example, the region of interest can have a predefined length of about 50-200 pixels and a predefined width of about 10-50 pixels, among others, which can be positioned on the detector based on the detected signal from a luminophore(s) disposed in a corresponding examination site (and/or based on detection of a light beam from the site; see below). Alternatively, the length and/or width of the region of interest can be set based on the detected signal from the luminophore (and/or based on detection of a light beam from the site; see below).

Figure 6:
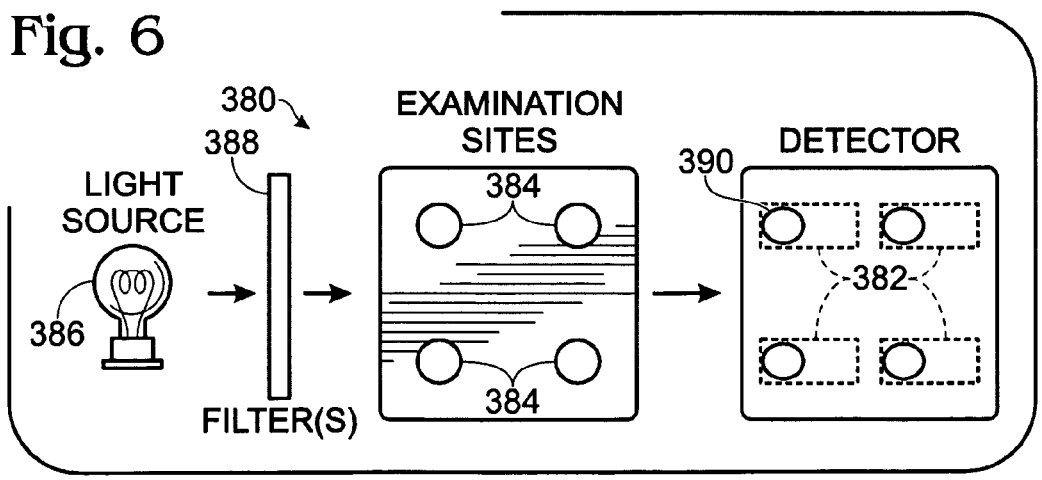
FIG. 6 is a schematic view of selected portions of another exemplary spectral imaging system illustrating assignment of regions of interest using filtered light, in accordance with aspects of the present teachings.

FIG. 6 shows selected portions of another exemplary spectral imaging system 380 illustrating assignment of regions of interest 382 using beams of light from examination sites (wells) 384. The beams can be created by a light source 386 and, optionally, at least one filter 388 disposed between the light source and the examination sites and/or between the examination sites and the detector. The light source can be part of the illumination system used to excite samples for light emission or can be a distinct light source used for calibration, such as a light source of narrow wavelength without a filter or a light source of broader wavelength with a filter. In some examples, the filter can be a band-pass filter that permits passage of a relatively narrow wavelength range of light. For example, here the filter produces a narrow enough wavelength range that light from each examination site is dispersed to produce a substantially circular well image 390 on the detector, with only slight elongation. Each region of interest 382 can be assigned according to the position of spectral well image 390 and/or according to a plurality of spectral well images created with different band-pass filters (e.g., a pair of band-pass filters to position each end of the region of interest). In some examples, the filter can permit passage of a range of wavelengths generally corresponding to opposing end positions of the region of interest (see FIG. 3).

IX. APPLICATIONS

Spectral imaging systems in accordance with the present teachings can be used for any suitable purposes, such as detecting and/or monitoring the occurrence of, and/or changes in, light received from one or more suitable samples.

The detection or monitoring of light can be performed qualitatively and/or quantitatively. Qualitative detection can include measurement of the presence or absence of a signal, and/or a change in a signal from present to absent, or absent to present, among others. Here, presence or absence can be in reference to a whole signal (such as any light) and/or a component of the signal (such as light of a particular wavelength (or wavelength region), polarization, and/or the like). Quantitative detection can include measurement of the magnitude of a signal, such as an intensity, wavelength, polarization, and/or lifetime, among others. The quantified signal can be used alone and/or compared or combined with other quantified signals and/or calibration standards. The standard can take the form of a calibration curve, a calculation of an expected response, and/or a control sample measured before, during, and/or after measurement of a test sample.

The detected or monitored light can be used for any suitable purpose, for example, to determine the amount, concentration, activity, and/or physical properties (including interactions) of an analyte (such as a photoactive analyte) in a sample. Here, the analyte can be the actual substance of interest and/or a reporter substance that reports on the actual substance of interest.

The substance of interest can be a reaction component. Exemplary reaction components can include an enzyme, enzyme substrate, enzyme product, and/or enzyme modulator (e.g., agonist and/or antagonist). Suitable reactions can occur in vivo and/or in vitro, for example, as part of a cell-lysis experiment and/or a polymerase chain reaction (PCR) preparation. Exemplary reaction components also can include precursors and/or products of a synthetic pathway, such as an amino acid, peptide, protein, nucleotide, polynucleotide, carbohydrate, fatty acid, lipid, and/or the like.

The substance of interest also can be the subject and/or product of a separatory process, such as on a chromatograph, gel, column, and/or the like. Here, the separatory process can include single processes, such as columns giving rise to fractions, and/or multiple processes, such as parallel lanes on a gel giving rise to sets of bands.

The substance of interest also can be the subject of a sequencing process, such as a peptide, protein, and/or nucleic acid (e.g., RNA and/or DNA) sequencing process. Here, the sequence can include amino acid sequence, nucleotide or base sequence (e.g., G, C, T, A, U, etc.), and so on, and the sequencing process can include generating fragments (or other derivatives) of the substance to be sequenced and labeling those fragments (before or after their generation) with different luminophores. Thus, in nucleic acid sequencing, the presence of a G, C, T, A, or U at a particular position in a substance of interest, or in a fragment or derivative thereof, can be determined by the identity of an associated luminophore.

The substance of interest also can be the subject of an identification, or affinity, process, such as a northern, western, and/or southern blot.

In some cases, the effect of some condition on the substance of interest can be determined, for example, by comparing results in the presence of the condition with predicted and/or measured results in the absence of the condition and/or the presence of another condition. Exemplary conditions can include presence or absence of a modulator (agonist or antagonist) or cofactor, and/or changes in temperature, concentration, pH, osmolarity, ionic strength, and/or the like.

The sample can include any appropriate material, with any suitable origin. For example, the sample can include a biomolecule, organelle, virus, cell, tissue, organ, and/or organism. A sample optionally can be a biological sample, such as a sample including test material from blood, urine, saliva, and/or mucous, among others. A sample optionally can be an environmental sample, such as a sample including test material from air, water, or soil, among others. A sample can be aqueous, and can contain biologically compatible organic solvents, buffering agents, inorganic salts, or other components known in the art for assay solutions. Suitable samples (or compositions) can include compounds, mixtures, surfaces, solutions, emulsions, suspensions, cell cultures, fermentation cultures, cells, suspended cells, adherent cells, tissues, secretions, and/or derivatives and/or extracts thereof.

The spectral imaging systems can be employed to assay samples, and particularly reactions within the samples, kinetically (i.e., at one or more times before the end of each reaction) and/or at steady state (i.e., after the endpoint of each reaction). With kinetic assays, the systems can monitor reactions in real time during the course of the reactions. In some examples, the spectral imaging systems can monitor two or more reactions within each sample concurrently to perform a multiplexed analysis. In particular, the progress of each reaction within a sample can be measured/monitored by a change(s) in light emission from the sample in a characteristic spectral region. For example, changes in emission from a distinct luminophore corresponding to each distinct reaction can be measured. The change in emission during the reaction can be caused by any suitable mechanism, including creation of the luminophore, degradation of the luminophore, structural modification of the luminophore, a change in the environment around the luminophore (such as its spacing from a donor or quencher), and/or a change (increase/decrease) in the energy transfer efficiency of an energy transfer pair including the luminophore.

In exemplary embodiments, the spectral imaging systems can be employed to detect and/or quantify two or more different nucleic acids (e.g., DNA or RNA) in each sample. For example, the nucleic acids can be quantified according to the rate at which they can be amplified detectably from the sample by an amplification reaction in which the nucleic acids are copied exponentially and/or linearly. Any suitable amplification approach can be used, including approaches that rely on thermal cycling (such as the polymerase chain reaction (PCR)) and/or that are substantially isothermal (such as Nucleic Acid Sequence-Based Amplification (NASBA), Loop-Mediated Isothermal Amplification (LAMP), Rolling Circle Amplification (RCA), Self Sustained Sequence Replication (S3R), Strand Displacement Amplification (SDA)), and/or the like. In some cases, probes/primers for different nucleic acid analytes in a sample can be labeled with a different luminophore and a quencher/energy transfer partner of the luminophore. Hybridization of a probe/primer to the analyte (e.g., with a molecular beacon probe) and/or cleavage (such as enzymatically) of the luminophore and/or quencher as a result of hybridization can produce a change in light emission from the luminophore. A suitable assay, the TaqMan® assay, that can quantify nucleic acids according to the rate of change in light emission is available from Applied Biosystems. Further aspects of amplification based assays are described below in Example 9.

The apparatus and methods described herein generally can be used with any suitable optically active composition (sample), for any suitable purpose. These compositions can include light-emitting, light-transmitting, light-absorbing, light-scattering, and/or light-reflecting compositions. Exemplary compositions can include single moieties and/or mixtures of two or more moieties capable of producing light at one or more wavelengths. The ability to separate colors described herein is particularly useful for single moieties that emit at two or more distinguishable wavelengths, and/or mixtures of moieties that collectively emit at two or more distinguishable wavelengths.

Exemplary compositions can be photoluminescent and/or chemiluminescent, among others. Photoluminescent sources produce photoluminescence light in response to illumination with suitable excitation light. Photoluminescence can include fluorescence (i.e., light produced by a singlet-to-singlet electronic transition) and/or phosphorescence (i.e., light produced by a triplet-to-single electronic transition), among others. Chemiluminescent sources produce chemiluminescence light associated with a chemical reaction (e.g., as part of a reaction that produces an intermediary or product in an excited electronic state that subsequently decays by production of light). Chemiluminescence can include bioluminescence (i.e., light produced by a biological reaction), among others.

Exemplary compositions can be naturally and/or artificially occurring. Naturally occurring compositions can include green fluorescent protein (GFP), phycobiliproteins, luciferase, and/or their many variations, among others. Artificially occurring compositions can include, for example rhodamine, fluorescein, FAM™/SYBR® Green I, VIC®/JOE, NED™/TAMRA™/Cy3™, ROX™/Texas Red®, Cy5™, and/or semiconductor nanocrystals, among others. Suitable natural and artificial compositions are disclosed in the following publication, among others, which is incorporated herein by reference: Richard P. Haugland, Handbook of Fluorescent Probes and Research Chemicals ($6^{th}$ ed. 1996).

X. EXAMPLES

The following examples describe selected aspects of the present teachings, including exemplary systems, methods, and algorithms for spectral imaging of samples. These examples are included for illustration and are not intended to limit or define the scope of the present teachings.

Example 1

Exemplary Dispersion Element Configurations

Figure 7:
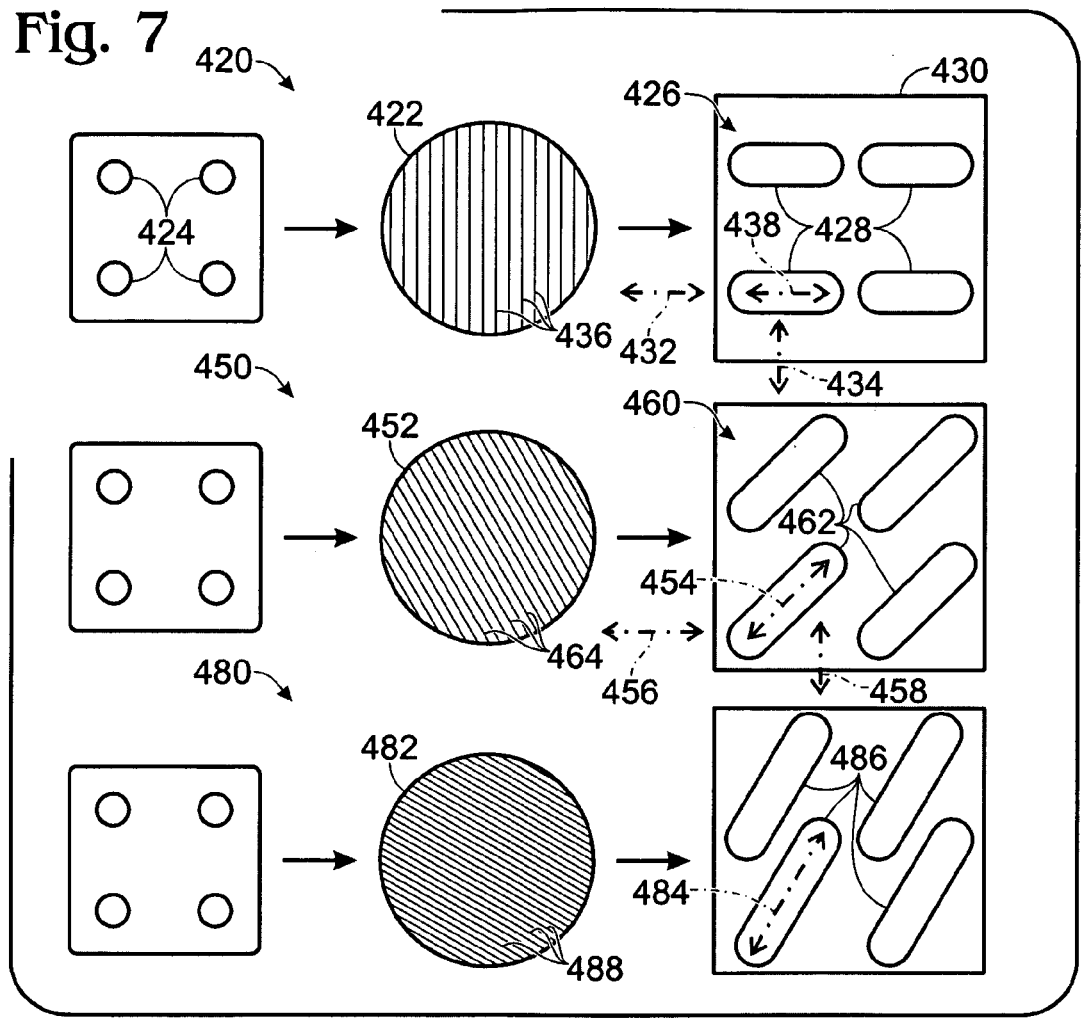
FIG. 7 is a schematic view of selected portions of exemplary spectral imaging systems having diffraction gratings disposed at different angles and having different line densities on each grating, in accordance with aspects of the present teachings.

This example describes exemplary spectral imaging systems 420, 450, 480 having distinct configurations of dispersion elements; see FIG. 7.

Imaging system 420 can include a dispersion element, namely a grating 422, that disperses light from a two-dimensional array of wells 424 to produce a corresponding array 426 of spectra 428 detected by a detector 430. The spectra can be arranged in rows and columns parallel to orthogonal axes 432, 434 defined by the array of spectra and, if the array is not slanted, aligned with corresponding detector axes. Grating 422 can have lines 436 oriented to produce a spectral axis 438 that is parallel to one of the axes (here, axis 432) of array 426. Accordingly, the long axes of spectra 428 can be aligned along a row or column of spectra, limiting the length of a spectrum according to the spacing of spectra measured parallel to one of the orthogonal axes (here, measured between corresponding spectral positions along a row).

Imaging system 450 can include a grating 452 that is rotated relative to grating 422 of system 420, to define a spectral axis 454 that is oblique to orthogonal axes 456, 458 defined by an array 460 of spectra 462 produced from the wells. Accordingly, grating 452 can have a higher density of lines 464 than grating 422 such that spectra 462 extend farther parallel to the spectral axis than spectra 428 of system 420 extend parallel to spectral axis 438. Furthermore, spectra 462 can be aligned diagonally within the array to limit the length to which each spectrum can extend without overlap.

Imaging system 480 can include a grating 482 that is rotated relative to gratings 422 and 452 of respective systems 420 and 450, to define a spectral axis 484 that is oblique to the orthogonal axes defined by the array of spectra 486. Accordingly, grating 482 can be have a higher density of lines 488 than grating 452 such that the spectra extend even farther than spectra 462, for example, between spectra in an adjacent row, as shown here.

Example 2

Exemplary Spectral Imaging System with a Grism

Figure 8:
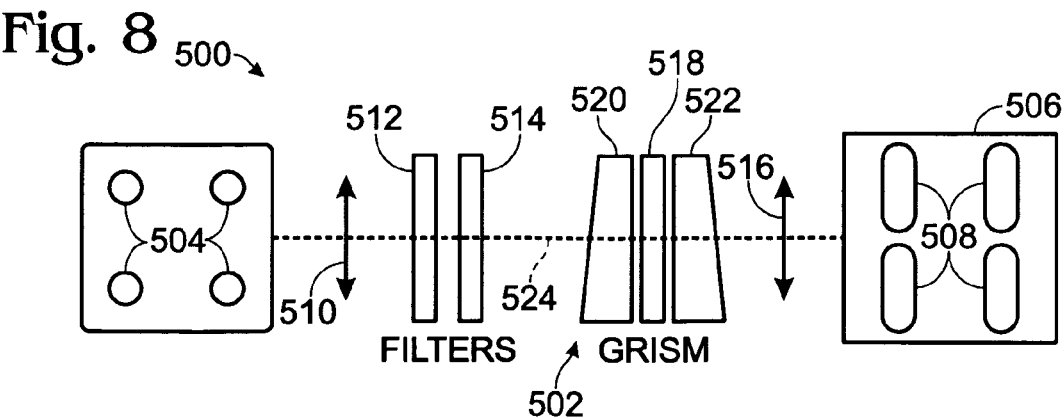
FIG. 8 is a schematic view of an exemplary spectral imaging system including a grism that positions spectra of interest generally on the optical axis of the system, in accordance with aspects of the present teachings.

This example describes an exemplary spectral imaging system 500 including a grism 502; see FIG. 8.

System 500 can disperse light emitted from an array of wells 504 and direct the dispersed light to a detector 506 to form a corresponding array of spectra 508 on the detector. The system can include an objective lens (or lens assembly) 510, filters 512, 514, grism 502, and detector lens (or lens assembly) 516 (e.g., a CCD camera).

The objective lens can receive emitted light from the wells, generally diverging light, and direct the light to long-pass filter 512 and short-pass filter 514, to select a suitable range of emitted light for dispersion. The objective lens can substantially collimate the light such that the filters receive collimated light. In some embodiments, the filters can be disposed elsewhere in the optical path, such as downstream or flanking the grism.

Grism 502 can include a grating 518 and one or more prisms, such as flanking symmetrical prisms 520, 522. The grating can disperse the filtered light and the prisms can shift the filtered/dispersed light laterally (and/or change the light angle), such that the dispersed light of interest remains substantially on optical axis 524 of the system.

Detector lens 516 can focus the dispersed, laterally shifted light onto detector 506. Nondispersed light can be disposed off (lateral to) the optical axis and can be received by a lateral region of the detector or can be undetected.

Example 3

Exemplary Spectral Imaging System with Off-Axis Imaging

Figure 9:
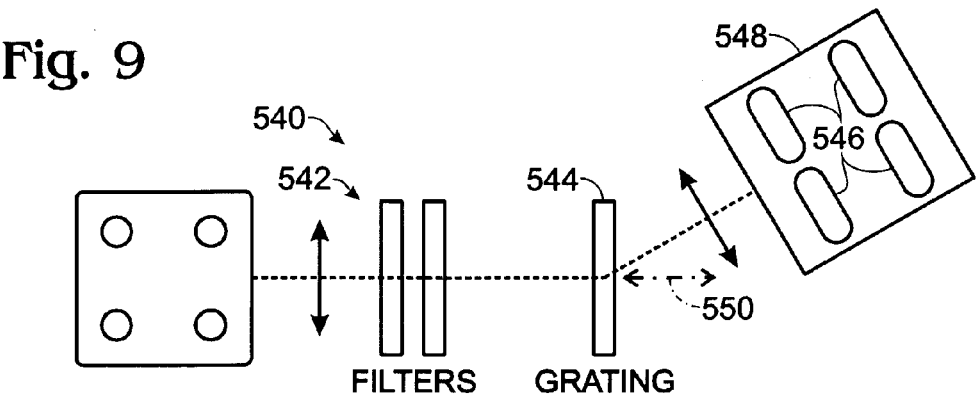
FIG. 9 is a schematic view of an exemplary spectral imaging system having a grating that positions spectra off the optical axis of the system, in accordance with aspects of the present teachings.

This example describes an exemplary spectral imaging system 540 that detects spectra off-axis; see FIG. 9.

Imaging system 540 can include an optical system 542 generally configured as described above for imaging system 500 (see FIG. 8). However, instead of a grism, the optical system can include only a grating 544. Accordingly, dispersed spectra 546 imaged by a detector 548 of the system can be disposed lateral to the optical axis 550 of the system. In contrast, nondispersed (zero order) light can be imaged substantially on optical axis 550, if suitable.

Example 4

Exemplary Spectral Imaging Systems with Optical Reduction

Figure 10:
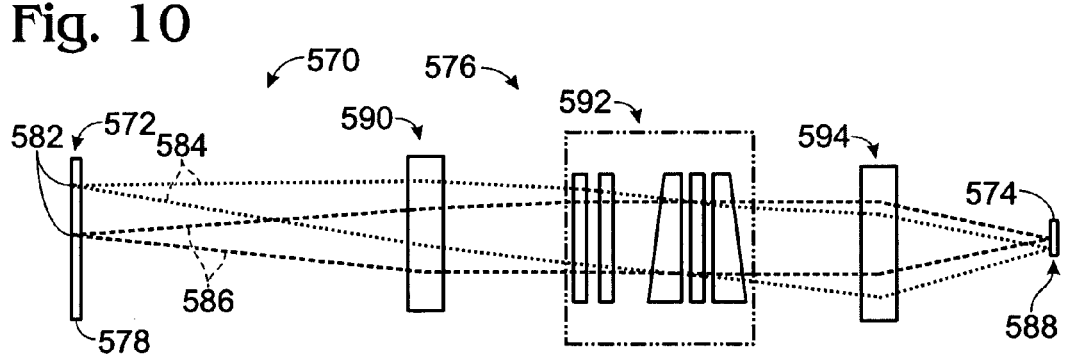
FIG. 10 is a side elevation view of selected portions of yet another exemplary spectral imaging system, particularly illustrating emitted light rays traveling from spaced positions in an examination area through an optical system and to more closely spaced positions on a detector after optical reduction, in accordance with aspects of the present teachings.
Figure 11:
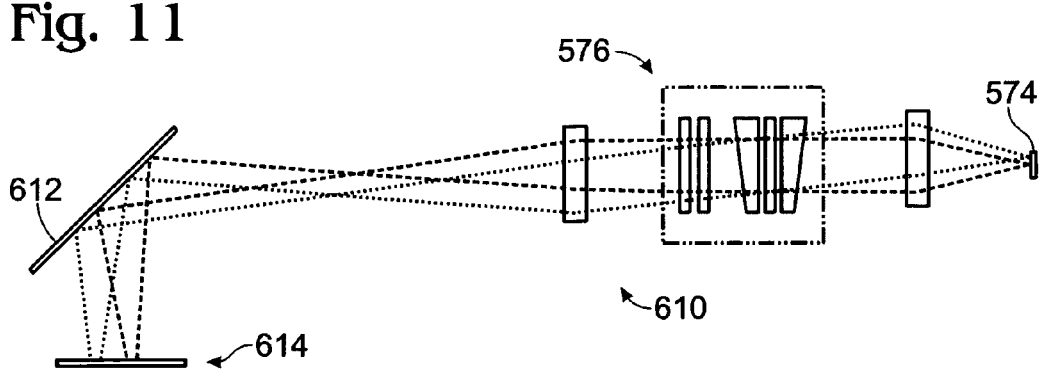
FIG. 11 is a side elevation view of selected portions of a modified version of the spectral imaging system of FIG. 10, in which the examination area is disposed off-axis from the optical system and detector, in accordance with aspects of the present teachings.

This example describes exemplary spectral imaging systems that optically reduce dispersed sample images; see FIGS. 10 and 11.

FIG. 10 shows selected portions of an exemplary spectral imaging system 570 with an on-axis configuration designed generally as indicated in Example 2. System 570 can include an examination area 572, a detector 574, and an optical system 576 operatively disposed relative to the examination area and the detector. In particular, the optical system can receive light from the examination area, collimate the light, filter the light, spectrally disperse the light, and re-focus the light onto the detector to produce optically reduced spectral images of the samples. In exemplary embodiments, the spectral images can be reduced about 2- to 10-fold or about 5-fold relative to the samples being imaged.

Examination area 572 can include a sample holder 578 including samples, such as samples 580, 582 disposed in an array. Emitted light from each sample, indicated at 584, 586 can be resolved by the optical system such that spectral images of the samples are correspondingly resolved on the detector, indicated at 588, after optical reduction.

Optical system 576 can include an objective lens assembly 590, a filter-grism assembly 592, and a detector lens assembly 594. Each assembly can employ a plurality of optical elements (or alternatively can be only a single element).

FIG. 11 shows selected portions of an exemplary spectral imaging system 610 that is a modified version of system 570 (see FIG. 10). System 610 can include a reflective optical element 612 that permits examination area 614 to be disposed off-axis from optical system 576 and detector 574.

Example 5

Exemplary Spectral Imaging Systems with Illumination Systems

Figure 12:
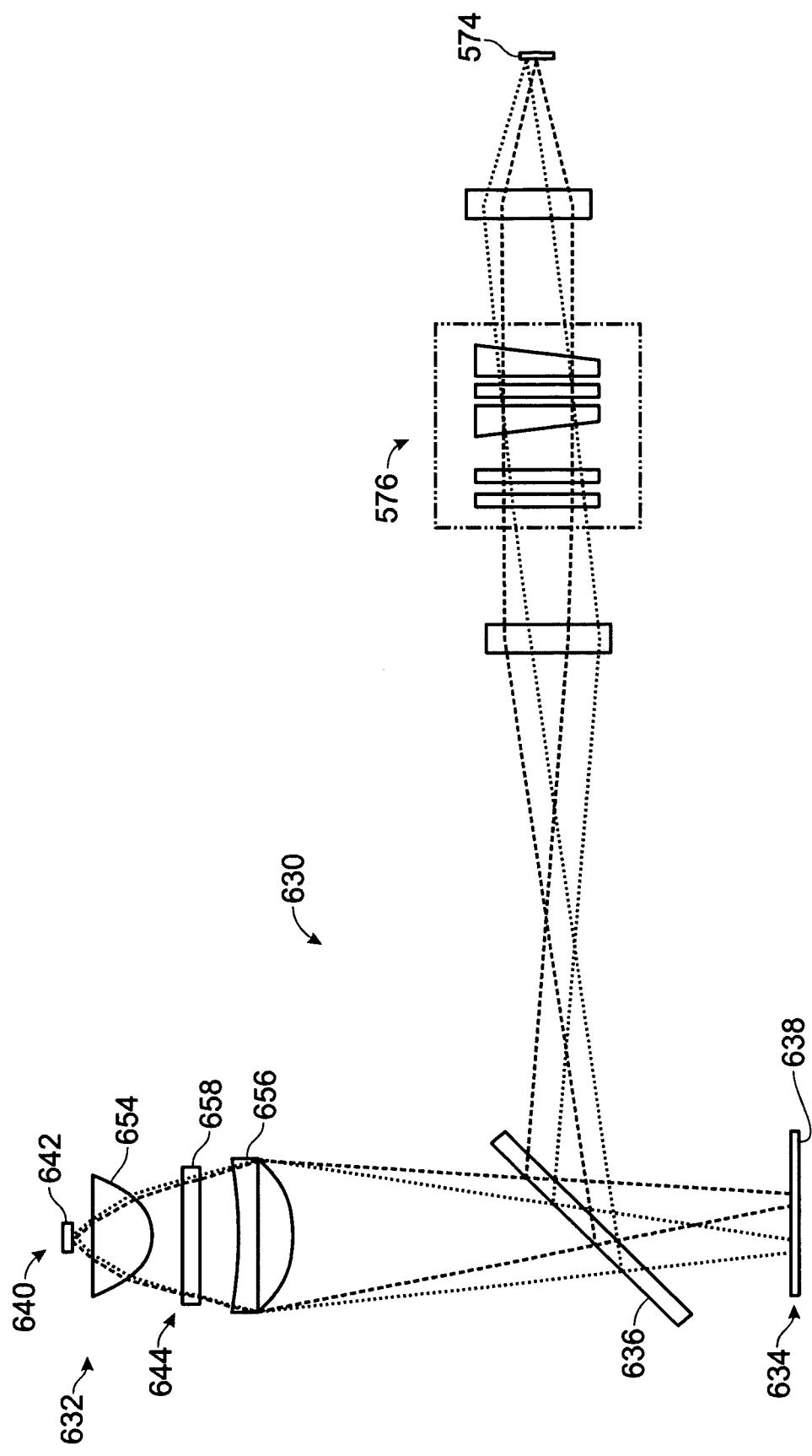
FIG. 12 is a side elevation view of selected portions of yet another modified version of the spectral imaging system of FIG. 10 that includes an exemplary illumination system, in accordance with aspects of the present teachings.
Figure 13:
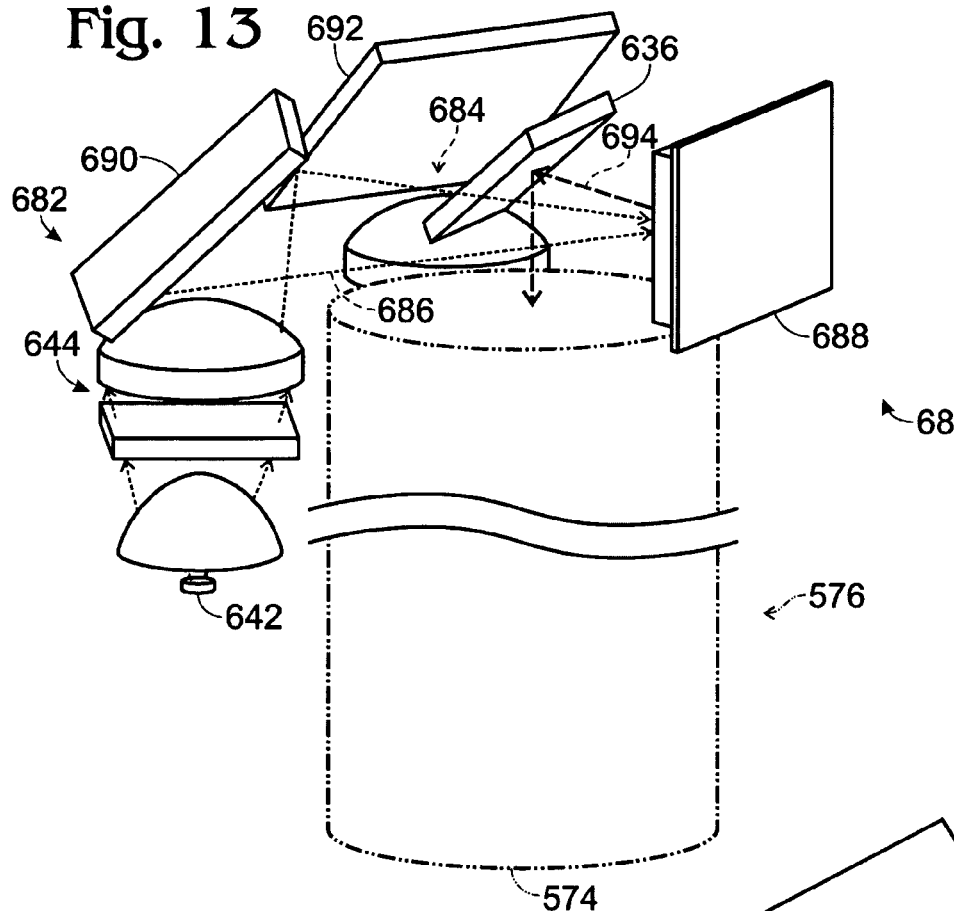
FIG. 13 is a partially schematic view of selected portions of an exemplary spectral imaging system that includes a pair of the illumination systems of FIG. 12, in accordance with aspects of the present teachings.
Figure 14:
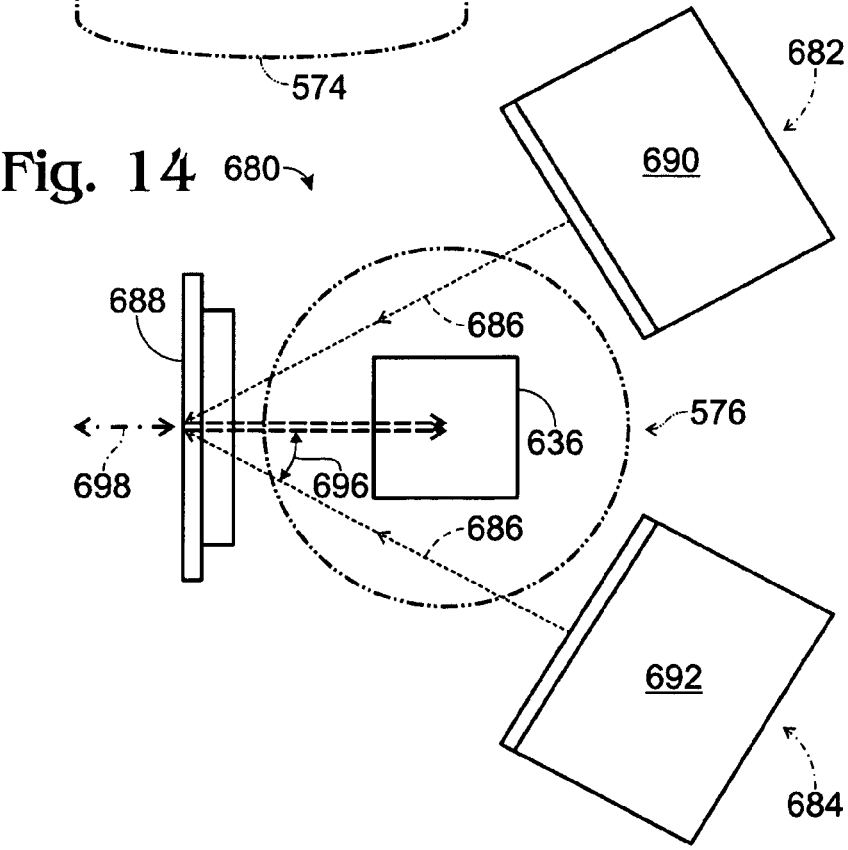
FIG. 14 is a plan view of the spectral imaging system of FIG. 13.

This example describes exemplary spectral imaging systems that include illumination systems; see FIGS. 12-14.

FIG. 12 shows a spectral imaging system 630 that is a modified version of systems 570 and 610 (see FIGS. 10 and 11). System 630 can include an illumination system 632 that illuminates examination area 634. The illumination beam can travel through a dichroic mirror 636 to a sample holder 638 disposed in the examination area, back to dichroic mirror, to optical system 576, and finally detector 574. The dichroic mirror can be configured to selectively reflect emitted light to optical system 576 (toward the detector) and to selectively transmit excitation light that is reflected back from the sample holder, to separate excitation and emission light.

Illumination system 632 can include a light source 640, such as a light-emitting diode 642, and source optics 644 that collect, homogenize, and focus the excitation light from the light-emitting diode (such that the cross-sectional size and/or shape of the light beam is changed in size and/or shape to substantially match the size and shape of the examination area). In exemplary embodiments, the source optics can include a collection element(s), a homogenization element, and any suitable additional optical elements such as refractive lenses 654, 656 and a filter 658, among others. In exemplary embodiments, the light source can be a LUXEON® III Blue LED.

FIGS. 13 and 14 show selected portions of an exemplary spectral imaging system 680 that is a modified version of system 630, with a plurality of illumination assemblies 682, 684 each corresponding to illumination system 632 of FIG. 12. Each illumination assembly can include a light source, such as light-emitting diode 642 and source optics 644. However, excitation light 686 from each light source (rays from only the front light source are shown here to simplify the presentation) can be directed to a sample holder 688 via respective mirrors 690, 692, which can be symmetrically offset angularly from dichroic mirror 636 (and/or a spectrally nonselective mirror)(see FIG. 12 also). Emitted light 694 from the sample holder can be reflected by dichroic mirror 636 to emission optics 576 and ultimately to detector 574 (see FIG. 10 also). Each light assembly 682, 684 can illuminate the sample holder from any suitable angle 696 relative to an orthogonal axis 698 from an image plane defined by the sample holder (see FIG. 14). In some examples, angle 696 can be about 20-45 degrees, with exemplary embodiments having angles of 25, 30, 35, or 40 degrees (and thus a total angle between light excitation beams of 50, 60, 70, or 80 degrees). The imaging system thus can have two or more light assemblies of the same structure but disposed at different positions.

Example 6

Exemplary Sample Holders and Examination Assemblies

This example describes exemplary sample holders and examination assemblies that can be suitable for holding samples in an examination area of the spectral imaging systems of the present teachings; see FIGS. 15-19.

Figure 15:
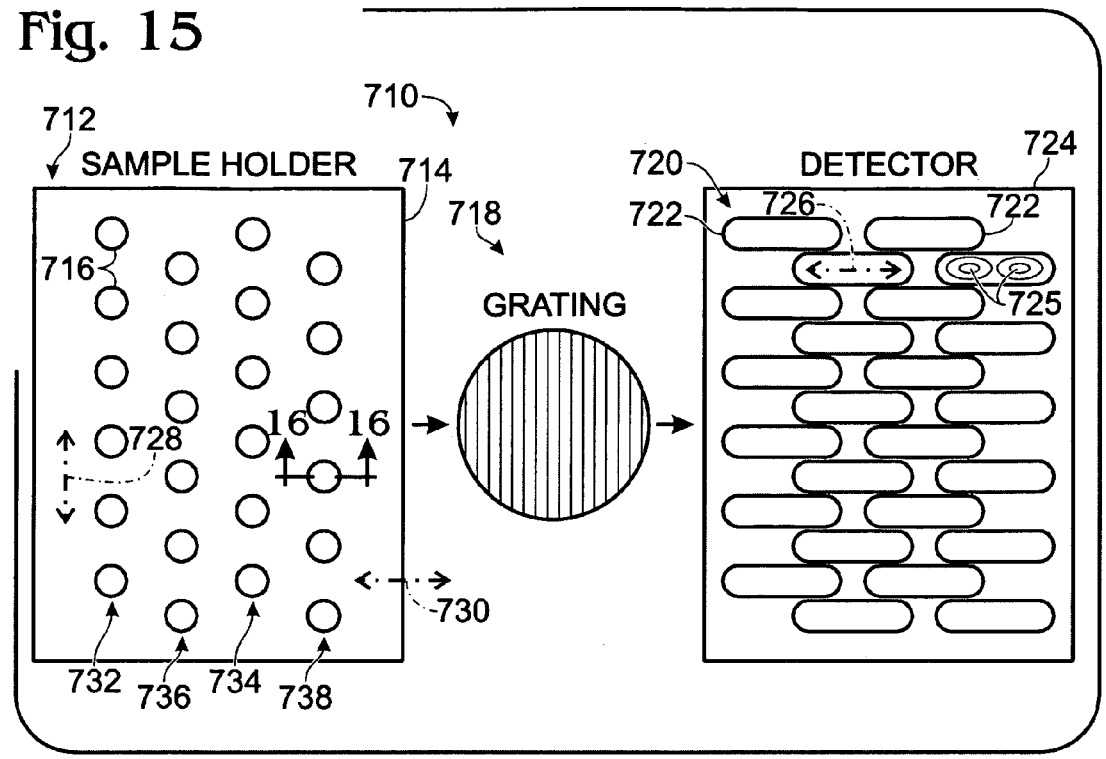
FIG. 15 a view of an exemplary spectral imaging system including an exemplary sample holder shown in plan and having a staggered arrangement of wells that results in a corresponding staggered array of spectral images on a detector of the system, in accordance with aspects of the present teachings.

FIG. 15 shows an exemplary spectral imaging system 710 including an exemplary sample holder 712 having a frame 714 with a staggered arrangement of wells 716 disposed in the frame. System 710 can include a dispersive optical system 718 that directs an array 720 of spectral images 722 of the wells to a detector 724. Exemplary spectral components 725 in one of the spectral images are shown here to improve clarity. The staggered arrangement can offer more distance between adjacent spectral images as measured parallel to a spectral axis 726 of the imaging system, than a corresponding nonstaggered arrangement of the wells. Accordingly, each spectral image can be lengthened by greater dispersion, without substantial overlap of adjacent (end-to-end) spectral images, for better resolution of spectral components within each spectral image.

The wells of the sample holder can be arranged in lines (e.g., columns in the present illustration) disposed parallel to orthogonal axes 728, 730. The orthogonal axes can be parallel (or oblique) to the perimeter of the frame. Wells in parallel lines can be offset from one another by any suitable fraction of the spacing between wells within the lines. For example, here, the wells in every other line (column) 732, 734 are offset from wells in the remaining lines (columns) 736, 738 by one-half the spacing between adjacent wells within the line.

The wells can have any suitable spacing measured parallel to each of axes 728, 730. For example, the wells can have a greater spacing measured parallel to one of the axes (here, axis 730) than measured parallel to the other axis (here, axis 728). For example, the wells can have about two, three, four, etc. times the spacing measured parallel to one of the axes relative to the other axis. This arrangement can allow assignment of more elongate rectangles as regions of interest on the detector. Furthermore, the spacing between adjacent lines of wells can be about the same as (or different than) the spacing of wells within each line. In some examples, the spacing between adjacent lines of wells and within each line can be a standard defined by the Society for Biomolecular Screening (SBS) as a suitable center-to-center spacing for microplate wells. Accordingly, the spacing can be 9 mm, 4.5 mm, or 2.25 mm, among others. This spacing can offer substantial advantages for fluid dispensing into the wells using automated (or manual) dispensers constructed according to an SBS standard. In exemplary embodiments, the line-to-line spacing (from center to center) is 4.5 mm, the diameter of each well is 2.0 mm with a volume capacity of about 1.5 µL, and the sample holder has a total of 24 wells in four lines/columns.

Figure 16:
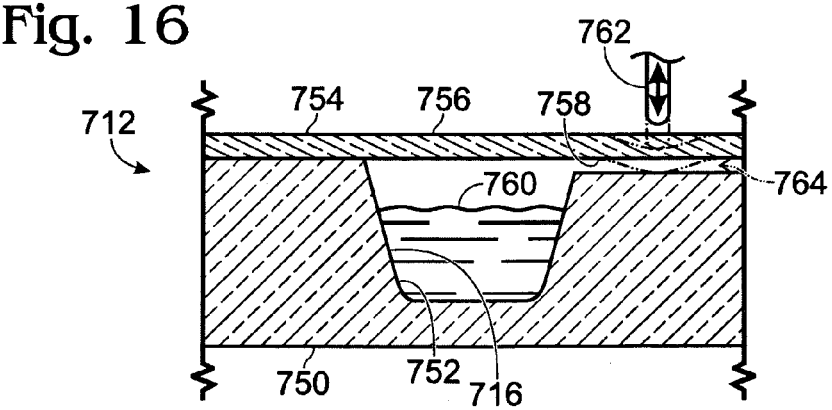
FIG. 16 is a sectional view of the sample holder of FIG. 15, taken generally along line 16-16 of FIG. 15.

FIG. 16 shows a sectional view of sample holder 712. The sample holder can include a body or body layer 750 defining an array of cavities 752 corresponding to wells 716. A cover layer 754 can be disposed over the cavities to provide a sealing element 756 for each well. Fluid access to the well can be provided by a channel 758 formed between the cover layer and the body. The channel can be in communication with a dedicated port for inputting fluid contents 760 into the well or can be in communication with a network of channels that extends to some or all of the other wells of the sample holder, for input of fluid contents to a plurality of wells via a common inlet port. In any case, the channel can be closed, and the well sealed, by a pin or stake 762 that engages the cover layer and deforms the cover layer, shown in phantom outline and indicated at 764, such that the cover layer contacts an apposed surface of the body. Stake 762 can extend upward (rather than downward as shown here) such that the sample holder is inverted relative to the configuration of FIG. 16 before placement in an examination area (e.g., see FIGS. 18 and 19).

In some embodiments, reagents can be dispensed into the wells before the cover layer is assembled with the body. For example, fluid dispensing equipment can be used to dispense aliquots of the reagents into the wells from above the body. In some examples, the reagents can then be dried. In any case, the cover layer can be assembled with the body, to protect the contents of the wells. The cover layer can be any suitable material, such as a pressure-sensitive adhesive layer.

Figure 17:
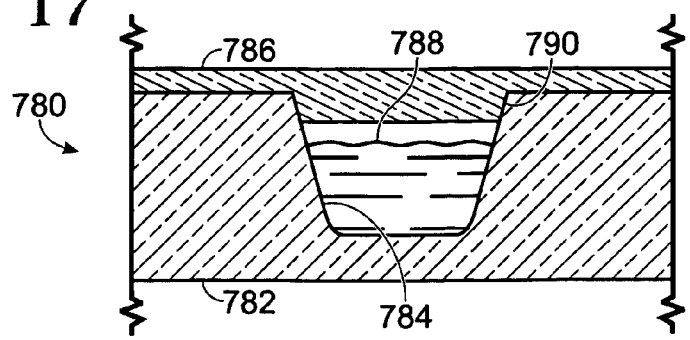
FIG. 17 is a sectional view of another exemplary sample holder, taken generally as in FIG. 16, in accordance with aspects of the present teachings.

FIG. 17 shows a sectional view of another exemplary sample holder 780. The sample holder can include a body 782 defining an array of cavities or wells 784. Each well can be sealed by the same sealing element 786, which can be placed over the body after a sample 788 is disposed in each well. The sealing element can have a plug region 790 that fits into the well or can have a flat inner surface, among others. In other embodiments, the wells each can have a corresponding sealing element formed as a separate component.

FIG. 18 shows an exemplary examination assembly 810 for positioning samples in an examination area of an exemplary spectral imaging system, viewed from generally below the assembly, with the assembly in an exploded configuration. The examination assembly can include a receiver 812, a sample holder 814, a mask 816, and a window assembly 818 disposed, respectively, in a vertical arrangement as shown here. The window assembly can be optically transmissive to excited and/or emitted light, to permit epi-illumination of the sample holder through the window assembly. In addition, the window assembly can urge the receiver, the sample holder, and mask together, such as by applying a weight to the mask, to maintain consistent engagement between these structures, for optical and/or thermal purposes, among others.

FIG. 19 shows receiver 812, sample holder 814, and mask 816 in an exploded configuration, as viewed from above and to the side of these structures.

Receiver 812 can provide a stage on which the sample holder is positioned. Accordingly, the receiver can define an examination area 820 in which the sample holder is received. The receiver thus can have a generally planar top surface with projections extending upward therefrom. The projections can include positioning pins 822 received in respective openings 824, 826 of the sample holder and mask, to restrict lateral movement of the sample holder and mask. The projections also can include an array of stakes 827 (also see stake 762 of FIG. 16) positioned to block channels in the sample holder (e.g., a channel similar to channel 758 of FIG. 16) when the sample holder is engaged with the receiver. The receiver can be a thermally conductive member, such as a metal plate or block. Accordingly, the receiver can be operatively coupled to a thermal control system, to transfer thermal energy between the thermal control system and the sample holder, for heating and cooling the sample holder, thereby providing temperature regulation of the samples therein.

Sample holder 814 can provide an array of wells 840. The wells can be accessed by a common inlet port 842 (see FIG. 18) for addition of the same test material to some or all of the wells. Accordingly, the port can communicate with some of all of the wells by a network of channels 844 (e.g., similar to channel 758 of FIG. 16), which can be closed by stakes 827 when the sample holder is aligned with the stakes by mating with pins 822 and urged against receiver 812. In some embodiments, the sample holder can have at least two inlet ports, such as a first inlet port for introduction of a test material, and at least a second inlet port for introduction of a control material. The sample holder can be rectangular, with a thickness that is substantially less than its length and width, to provide a card-shaped holder.

Mask 816 can provide an array of light-transmissive apertures 846. The apertures can be arranged in alignment with wells 840 of the sample holder when the mask is mated with the receiver via pins 822. The mask can be opaque around the apertures, to avoid detection of optical signals from positions between the wells of the sample holder (e.g., from channels 844). The mask can be a relatively thin, opaque plate with an array of cylindrical through-holes. Alternatively, the mask can be thicker, as shown here, with apertures that are frustoconical or cylindrical through-holes, among others. Accordingly, with a thicker (or thinner) mask, the opaque regions can be formed using an opaque material to form the body of the mask. Alternatively, the apertures can be optical apertures, rather than through-holes, formed, for example, by applying an opaque coating to one or both sides of a light-transmissive body, without creating through-holes, to form a patterned array of openings in the coating.

Example 7

Exemplary Algorithms for Assigning Regions of Interest

Figure 20:
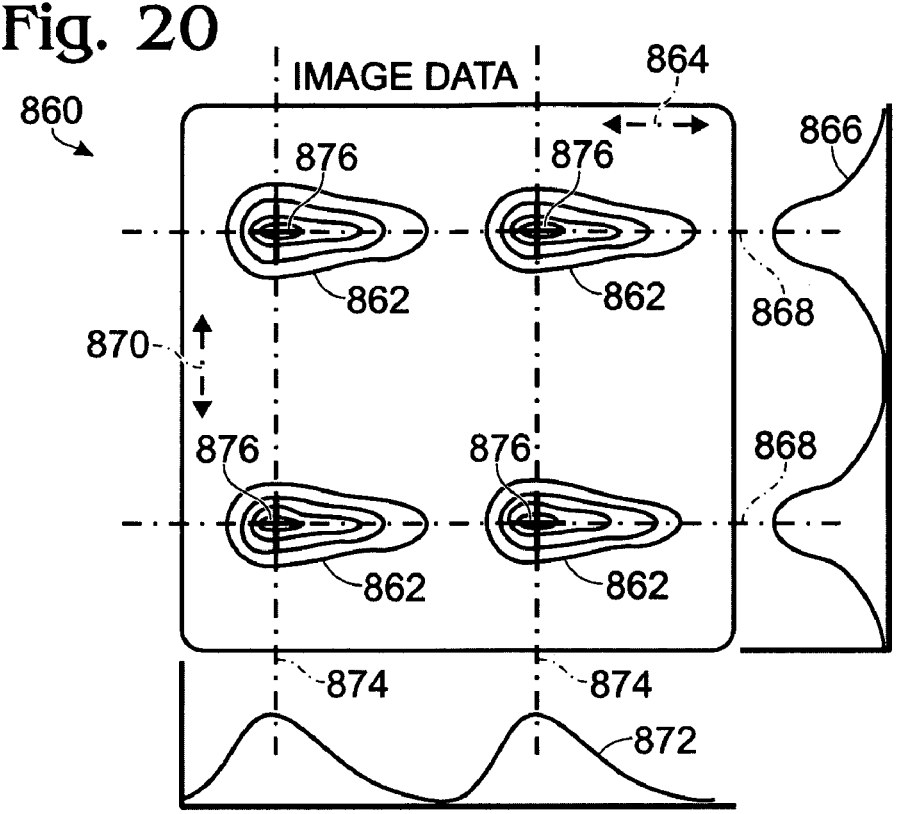
FIG. 20 is a representation of exemplary image data collected by a spectral imaging system and of exemplary processing of the image data to identify features of the image data, in accordance with aspects of the present teachings.
Figure 21:
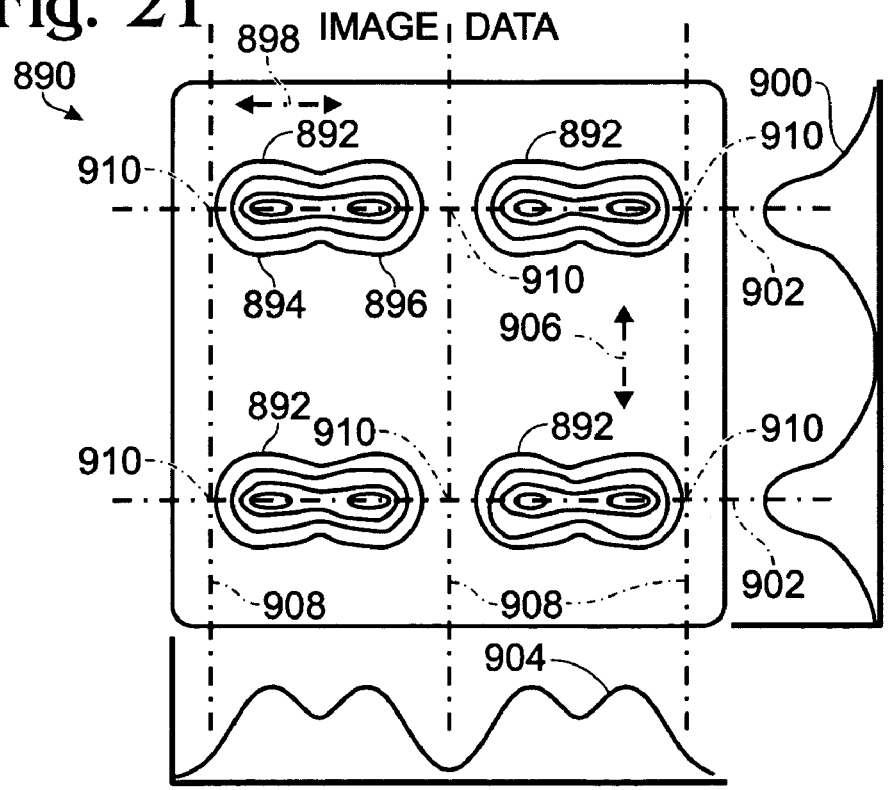
FIG. 21 is another representation of exemplary image data collected by a spectral imaging system and of additional or alternative exemplary processing of the image data to identify features of the image data, in accordance with aspects of the present teachings.
Figure 22:
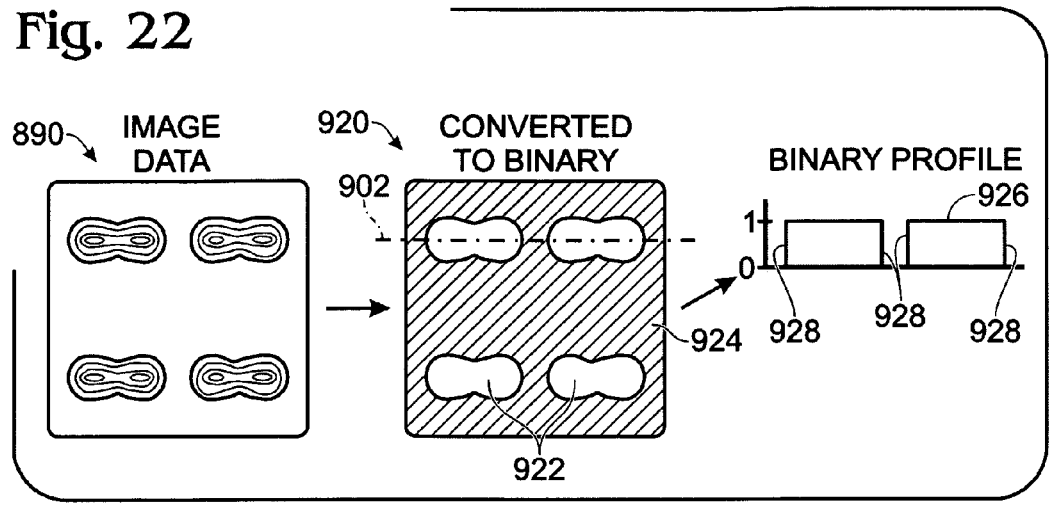
FIG. 22 is a representation of the image data of FIG. 21 illustrating exemplary conversion of the image data to a binary form by thresholding, to facilitate identification of feature boundaries within the image data, in accordance with aspects of the present teachings.

This example describes exemplary algorithms for processing image data to assign regions of interest; see FIGS. 20-22.

FIG. 20 shows an image representation of image data 860 collected by an exemplary spectral imaging system. Image data 860 can describe an array of spectral images or spectra 862 (e.g., first order images) of wells of a sample holder holding the same dye in an examination area of the imaging system.

One or more algorithms can be used to process the image data for identification of features within the image data. The features can be maxima, minima, transitions, and/or thresholds, among others, within the image data and can be spectral (and/or nonspectral) features produced by dispersed (and/or nondispersed) light. The features can be arranged in a feature array in correspondence with a sample/well array that produced the features. Accordingly, the algorithms can search for features based on predefined parameters regarding expected relative feature positions within the image data, to reduce identification of spurious features.

The image data can be collapsed in a direction parallel to one or more axes to facilitate feature identification. For example, the image data can be collapsed (summed) parallel to a first orthogonal axis 864, to provide a profile 866 that facilitates identification of center positions 868 of rows of features within the image data, as intensity maxima. Alternatively, or in addition, the image can be collapsed (summed) parallel to a second orthogonal axis 870, to provide a profile 872 that facilitates identification of column positions 874 of spectral maxima within the image data. Feature maxima 876 thus can be identified approximately at the intersection of the row and column positions determined.

Each profile 866, 872 can be processed in any suitable way to obtain the maxima. For example, the local maxima of these profiles can found by first smoothing the profile (e.g., by using a Savitzky-Golay filter, an averaging filter, etc.) and applying a peak-finding algorithm (e.g., finding where the slope is zero), to find the approximate coordinates within the image data for each spectrum. The approximate coordinates can be refined by doing a local search for the area of highest intensity around these row and column positions. Further aspects of searching for local maxima iteratively (e.g., to identify centroids and/or intensity midpoints), are described in the patent applications listed above under Cross-References, which are incorporated herein by reference.

Approximate and/or refined feature positions within the image data can be used to assign regions of interest within the image data and thus relative to a detection area that detected the image data. For example, features 876 can be used to assign the locations of one or both sides and/or ends of regions of interest that include the features. The boundaries of each region of interest can be assigned by, for example, setting the boundary at predefined numbers of pixels from the feature position parallel to axes 864 and 870 (such as based on a calculated or measured wavelength per pixel relationship for the detector along a spectral axis). For example, a shorter wavelength end of each region of interest can be defined by subtracting a predefined number of pixel positions parallel to spectral axis 864 (to move to the left in this figure), and a longer wavelength end of each region of interest can be defined by adding a different (or the same) number of pixel positions parallel to spectral axis 864 (to move to the right in this figure). Similarly, the side positions of each region of interest can be set by moving parallel to spatial axis 870 from each feature position (up or down in this figure) by the same (or a different) number of pixel positions. In some embodiments, spectra from a single dye can be used to set only one of the two spectral endpoints of each region of interest (e.g., the shorter wavelength endpoint using the spectra shown here). Alternatively, or in addition, one or more boundaries of each region of interest can be assigned based on where the signal falls off from the intensity maxima to a threshold amount (see below).

FIG. 21 shows another image representation of image data 890 collected by an exemplary spectral imaging system. Image data 890 can describe an array of spectral images or spectra 892 (e.g., first order images) of wells of a sample holder holding the same mixture of two dyes in an examination area of the imaging system. Accordingly, one of the dyes can be used in defining the position of the shorter wavelength end of each region of interest, and the other dye can be used in defining the position of the longer wavelength end of each region of interest. However, the presence of dyes producing overlapping spectral components 894, 896 of each composite spectrum can make identification of maxima less reliable along a line parallel to a spectral axis 898 of the image data. Accordingly, a profile 900 can be generated by summing parallel to spectral axis 898 and then analyzed to identify row positions 902 within the image, as described above in relation to FIG. 20. A profile 904 also can be generated by summing orthogonal to spectral axis 898, parallel to a spatial axis 906. Profile 904 can be analyzed to identify column positions 908 that are intensity minima. Feature minima 910 can be identified as the coordinates at which positions 902 and 908 intersect. Regions of interest then can be assigned based on the positions of the feature minima, generally as described above for feature maxima.

FIG. 22 shows image data 890 of FIG. 21 being processed, in part, by thresholding to facilitate identification of features within the image data. Row position 902 can be identified as described above in relation to FIGS. 20 and 21. Threshold positions along each row can be identified by converting image data 890 to binary image data 920 according to a threshold (generally near background). Accordingly, the threshold can be predefined or defined based on the image data. In any case, pixels with an intensity above the threshold can be set to one (or zero), indicated at 922, and pixels with an intensity below the threshold can be set to zero (or one), indicated at 924. A resulting binary profile 926 taken at row position 902 can be used to set positions 928 of opposing ends of each region of interest within the row.

In other embodiments, regions of interest can be assigned based on changes to sample spectra produced in a kinetic assay, rather than (or in addition to) being pre-assigned via calibration standards. For example, image data of the samples can be collected at two or more distinct times and changes to spectral images can be revealed by determining a difference image, such as by subtracting image data from the beginning of the reaction from image data collected at a later time point or endpoint of a reaction. Accordingly, regions of interest can be assigned in such subtracted image data by finding maxima, minima, transitions, thresholds, and/or the like, as described in this example and elsewhere in the present teachings. Further aspects of dynamically assigning regions of interest are described in the following patent application, which is incorporated herein by reference: U.S. Provisional Patent Application Ser. No. 60/817,833, filed Jun. 29, 2006, titled "TWO-DIMENSIONAL SPECTRAL IMAGING SYSTEM," and naming Dar Bahatt and Chirag Patel as inventors.

Example 8

Exemplary Use of Fiducials to Assign and/or Reposition Regions of Interest

Figure 23:
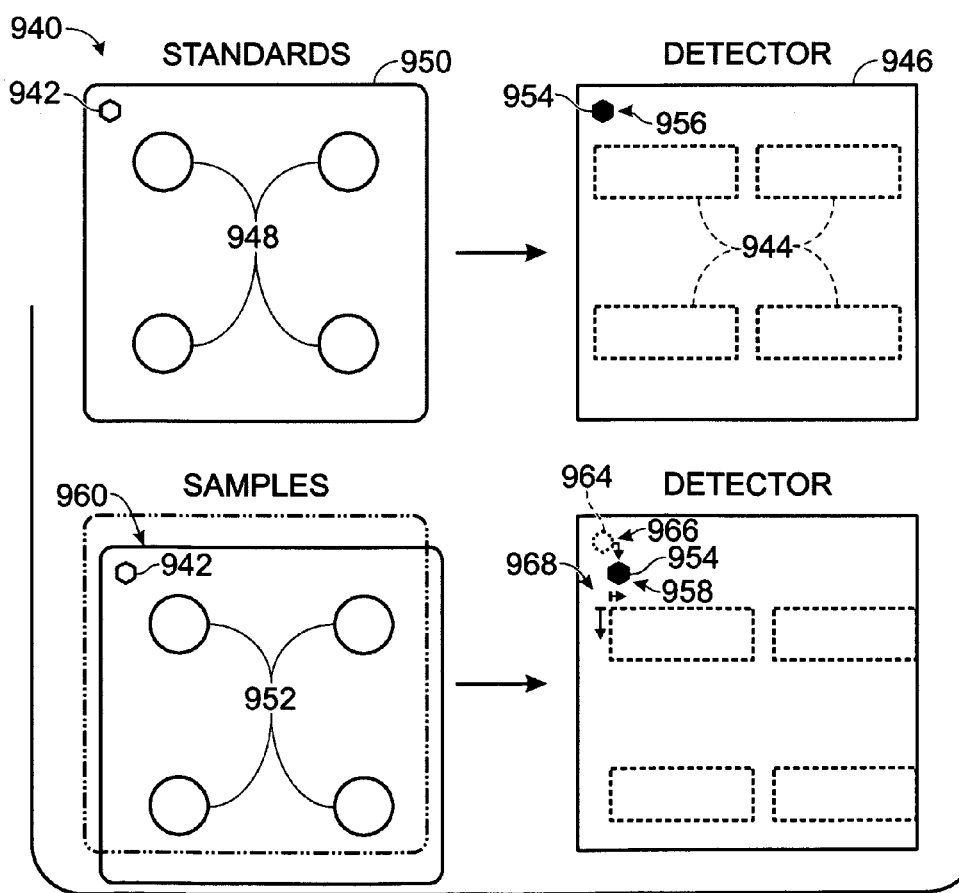
FIG. 23 is a schematic view of selected portions of a spectral imaging system that uses a fiducial to correct for variability of sample holder/well position in an examination area of the system (and/or variability of region of interest position on the detector), in accordance with aspects of the present teachings.

This example describes an exemplary use of fiducials to facilitate assigning and/or repositioning regions of interest; see FIG. 23.

FIG. 23 is a schematic view of selected portions of a spectral imaging system 940 that uses a fiducial 942. The fiducial can be used to correct for variability of sample holder and/or well positioning in the examination area of the system relative to the system optics and/or the detector. Furthermore, in some cases, the fiducial can be used to correct for changes to the system optics and/or to the relation of the system optics to the examination area and/or detector, among others, during use, transport, storage, service, etc., of the system.

Regions of interest 944 can be assigned on a detector 946 (and thus in image data detected by the detector) using standards 948 disposed in wells of a sample holder 950 disposed in the examination area. Fiducial 942 can be disposed at the same fixed position relative to the wells of a sample holder used to hold the standards and also relative to wells used to hold test samples 952. Accordingly, detection of light from the fiducial on the detector, indicated at 954, can provide a reference position(s) 956 (standards) or 958 (samples) within the image data.

The reference position can be used to for determining where the wells are positioned in the examination area and/or to adjust for changes in well position produced with variability in sample holder placement into the examination area, among others. For example, samples can be placed into the examination area offset, indicated at 960, relative to a position (dashed) of the sample holder during calibration and assignment of regions of interest. Accordingly, the original detected fiducial position, indicated as a dashed outline 964 on the sample image, is shifted translationally, indicated at 966, to new detected fiducial position 958. Accordingly, the fiducial can be detected in an offset position on the detector. The regions of interest can be moved, indicated at 968, based on the offset position measured for the fiducial.

The fiducial can have any suitable structure. For example, the fiducial can be a reflective region of the sample holder, such as a mirror to reflect excitation light, or a transmissive region of the sample holder, such as a through-hole. Alternatively, the fiducial can be luminescent, to emit light when illuminated. For example, the fiducial can be a luminescent area with a narrow band of emission, to provide a well-defined spectral image of the fiducial on the detector, generally a spectral image of the same (and/or different) diffraction order as spectral images of the wells on the detector. The fiducial can have any suitable size, for example, a relatively small area to provide a relatively sharp fiducial image on the detector that defines a position more precisely.

In some examples, the fiducial image can be detected on the detector as nondispersed light from fiducial 942. Accordingly, the fiducial can be provided by one of the wells, a row or column of the wells, and/or all of the wells.

The fiducial can have any suitable position. The fiducial be disposed within the array, such as between wells, outside of the array, as shown here, or can be part of the array itself, such as when nondispersed light serves as a positional reference or datum. to facilitate identification, particularly automatically, of higher order spectral images. For example, the imaging system can use an algorithm to identify regions of interest of the detector for first order spectral images based on extrapolation from the position(s) of the zero order nonspectral well images on the detector. The sample holder can have only one fiducial imaged by the detector, two or more fiducials (such as to correct for a rotational offset of the sample holder), and/or the like.

Example 9

Exemplary Methods of Sample Analysis

This example describes methods of sample analysis involving linear decomposition of composite sample spectra; see FIGS. 24-27.

Figure 24:
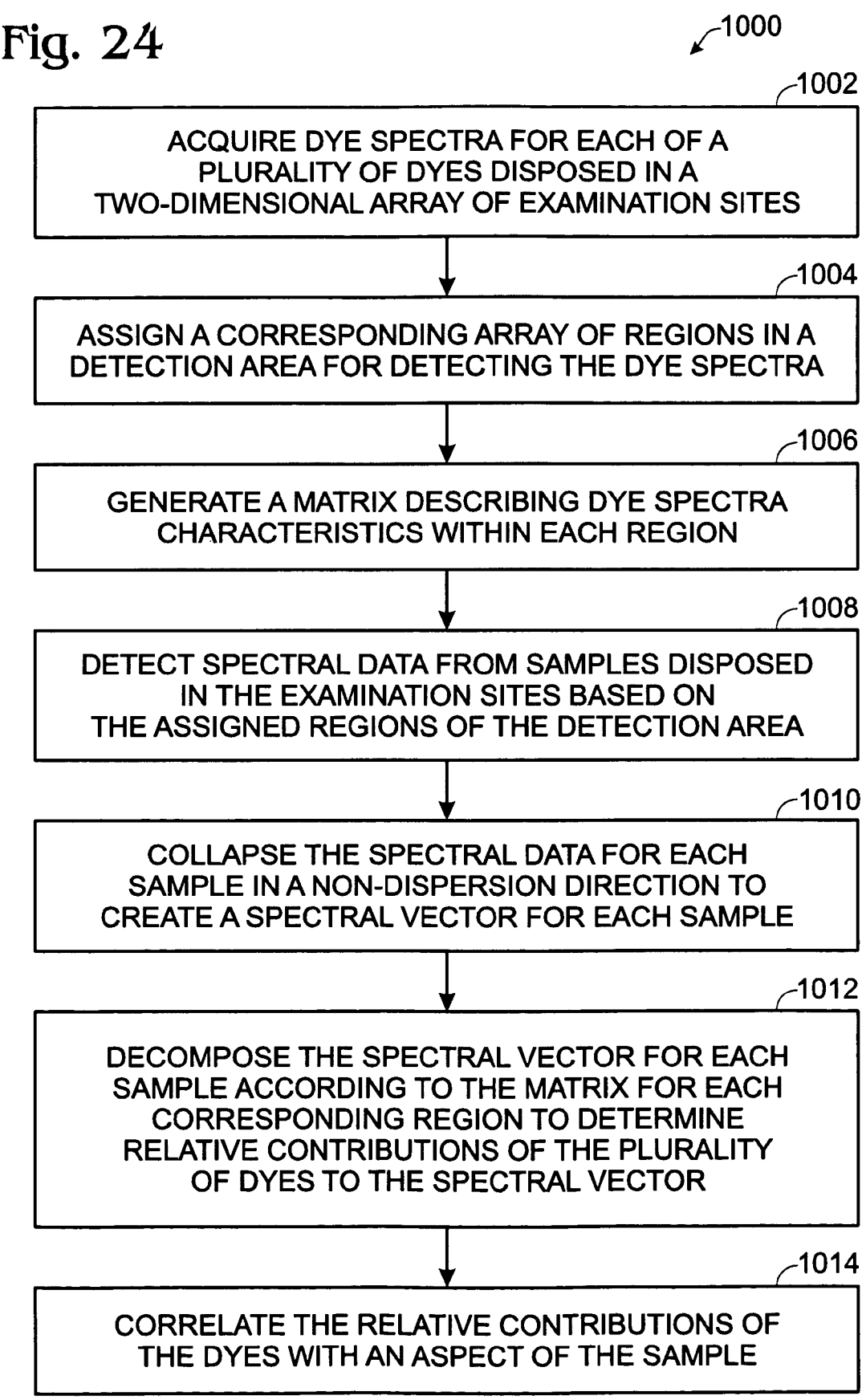
FIG. 24 is a flowchart listing steps for performing an exemplary method of sample analysis using a plurality of dyes, in accordance with aspects of the present teachings.

FIG. 24 shows a flowchart 1000 listing exemplary steps for performing a method of sample analysis using a plurality of dyes. The steps listed can be performed in any suitable order, in any suitable combination, and any suitable number of times.

Dye (or luminophore) spectra can be acquired with a two-dimensional imaging system, indicated at 1002. The dye spectra can be acquired from a dye mixture or from dyes disposed serially in examination sites. In particular, the dyes can be disposed in sample holders with wells that place the dyes in areas large enough to create broadened dye spectra relative to the dye spectra produced from a point or line source with each dye.

Regions of interest for detecting the dye spectra can be assigned in a detection area of the imaging system, indicated at 1004. The regions of interest can be assigned based on detection of spectral images of wells holding the dyes themselves, wells holding other standards, and/or can be assigned based on other criteria.

A matrix describing characteristics of dye spectra within a region of interest can be generated, indicated at 1006, for each region of interest. The matrix, generally termed a calibration matrix, can correspond to profiles of spectral images of the dyes detected by the region of interest. Accordingly, the distribution of signal strength over the region of interest can be indicated for each dye spectrum.

Spectral data from samples disposed in the examination sites can be detected (and/or obtained) based on the assigned regions of interest of the detection area, indicated at 1008. The spectral data for each sample can correspond to a spectral image of the sample held by a well. The spectral data for the sample can be obtained in exact correspondence with a region of interest or can be shifted translationally or rotationally from the region of interest, for example, based on a fiducial(s) (e.g., see Example 8).

The spectral data for each sample can be collapsed parallel to a spatial axis of the data, indicated at 1010, generally by summing the data parallel to the spatial axis. Collapsing the spectral data can convert two-dimensional image data into one-dimensional data, namely, a spectral vector (a composite profile) for each sample.

The spectral vector for each sample can be decomposed, indicated at 1012. In particular, the spectral vector can be a linear combination of isolated ("pure") dye spectra, i.e., dye spectra measured without energy transfer (or other interference) between the dyes (and/or with a non-dye quencher). The calibration matrix of step 1006 can be used for linear decomposition, such as via multiplication by the pseudoinverse of the calibration matrix. Relative contributions of the plurality of dyes to the spectral vector/profile can be determined.

The relative contributions of the dyes to the spectral data can be correlated with an aspect of the sample, indicated at 1014. The aspect can be amount (e.g., presence/absence or level/concentration) of an analyte(s). In some examples, the aspect can be a plurality of aspects determined for the same analyte or for different analytes in the sample. Accordingly, the analysis can be a multiplexed assay of each sample, such as for the presence/absence and/or level/concentration of two or more distinct nucleic acid analytes.

Figure 25:
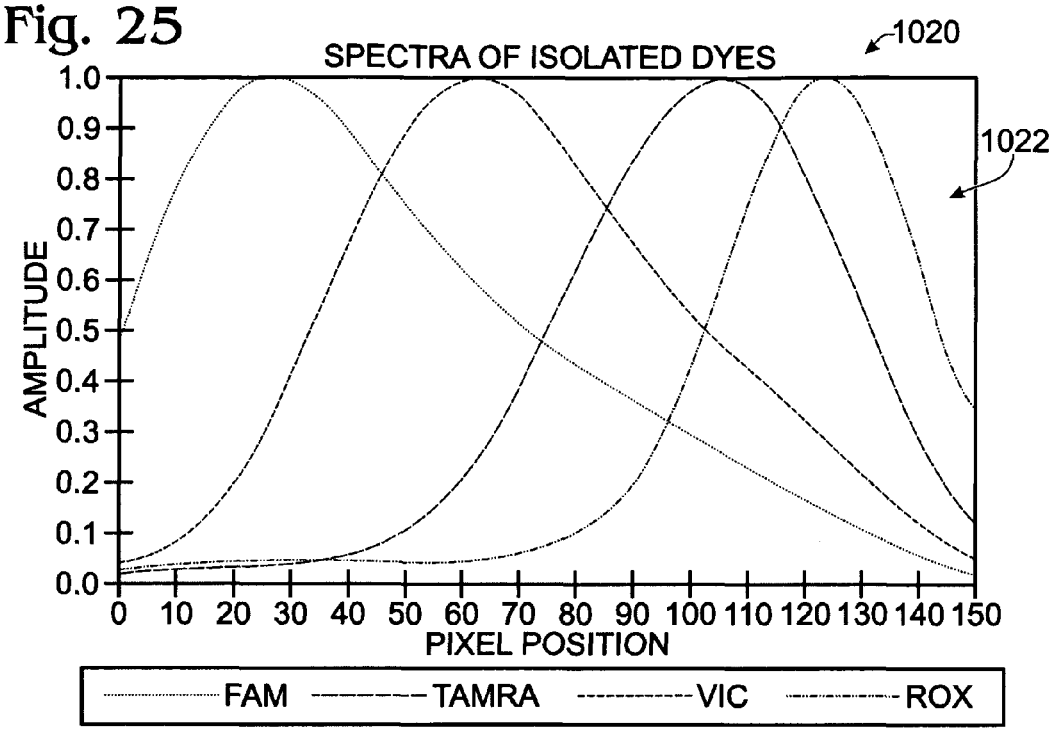
FIG. 25 is a graph of an exemplary calibration matrix for a set of dye spectra detected in the same region of interest of a detector of a spectral imaging system, in accordance with aspects of the present teachings.

FIG. 25 shows a graph 1020 of an exemplary calibration matrix 1022 for a set of isolated dye spectra detected in the same region of interest of a detector of a spectral imaging system. A sample with each indicated dye (i.e., FAM dye, TAMRA dye, VIC dye, and ROX dye) can be disposed in the same size/shape of well and in the same examination site of the imaging system for detection of the corresponding spectral image of the dye sample. The two-dimensional spectral data for each dye sample can be collapsed to one dimension, normalized (before or after collapse), and plotted according to pixel position along the spectral axis of the region of interest.

Figure 26:
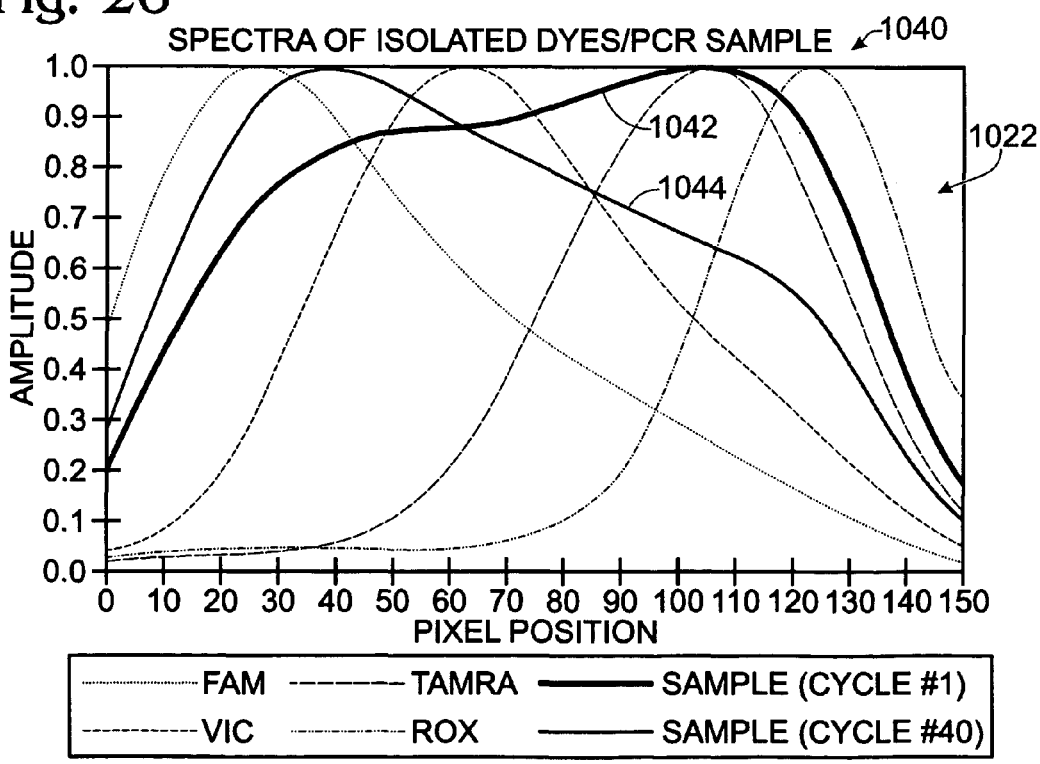
FIG. 26 is a graph of the calibration matrix of FIG. 25 and exemplary sample spectra detected in the same region of interest, either near the beginning or the end of thermal cycling for nucleic acid amplification of a sample, in accordance with aspects of the present teachings.

FIG. 26 shows a graph 1040 of the calibration matrix of FIG. 25 along with exemplary respective collapsed spectra 1042, 1044 for a test sample detected in the same region of interest, near the beginning (cycle 1) and end (cycle 40) of thermal cycling of the test sample. The test sample can be a reaction mixture for performing nucleic acid amplification by the polymerase chain reaction (PCR).

The sample can include a mixture of each of the dyes for which the calibration matrix was generated. In particular, the sample can include (1) TAMRA dye as a quencher by fluorescence resonance energy transfer (FRET) of FAM dye and/or VIC dye; (2) distinct nucleic acid probes each conjugated to FAM dye and TAMRA dye or VIC dye and TAMRA dye (or only one type of probe); and (3) ROX dye as an internal control (which should not change substantially during the reaction).

Generation of amplification product to which each probe binds can result in subsequent degradation of the probe by a polymerase in the reaction mixture. The polymerase can use the product at a template for further DNA synthesis. Degradation of the probe can reduce energy-transfer based quenching by TAMRA. Accordingly, degradation can produce an increase in the signal from FAM dye or VIC dye according to the probe degraded. For example, here, the signal for the test-sample spectrum at cycle one is strongest at about pixel position 110 (TAMRA peak) and weaker at pixel positions to the left of this pixel position (shorter wavelengths). In contrast, the signal for the test-sample spectrum at cycle forty is strongest at about pixel position 40 and relatively weaker at about pixel position 110, reflecting a decrease in energy transfer to TAMRA.

FIG. 27 shows an exemplary graph 1060 of the relative spectral contributions of the four indicated dyes to the composite spectra of the PCR sample described for FIG. 26. The spectra can be detected in the same region of interest, in real time, for example, as the sample is repetitively cycled thermally, to promote amplification of template. Alternatively, the spectra can be detected over time as the sample is held at the same temperature (e.g., during isothermal amplification or another type of chemical/binding reaction). The relative contributions of the four dyes to the composite spectra can be determined by linear decomposition of each composite spectrum using the calibration matrix of FIG. 25, and test-sample data at approximately the indicated cycle numbers to generate graph 1060. Here, VIC dye and FAM dye increase in intensity due to amplification of nucleic acid analytes to which the VIC-conjugated probe and the FAM-conjugated probe can bind. In addition, the intensity of the quencher dye TAMRA drops, and ROX dye provides a steady signal.

Example 10

Exemplary Broadening of Spectra

This example describes broadening of a dye spectrum for an exemplary spectral imaging configuration.

The system can have the following configuration. The size of a well image on the detector can be calculated as physical size (e.g., 0.5 to 5 mm diameter), multiplied by system magnification (e.g., 0.2), to give 0.1 to 1.0 mm. The size (length/width) of a pixel on the detector (e.g., a CCD camera) can be 10 μm. Accordingly, the well image size of 0.1 to 1.0 mm, which is equal to 100 to 1000 μm, can be divided by 10 μm per pixel, which gives 10 to 100 pixels. In exemplary embodiments, the wells each have a diameter of two millimeters, the diameter (2 mm) multiplied by the optical reduction (0.20) gives an image size of 0.4 mm. This image size (400 μm), with a detector of 10 μm per pixel, can give a size of 40 pixels over which a single wavelength of light from the well can be distributed along a line that is parallel the spectral axis of the detector. In exemplary embodiments, one pixel on the detector corresponds to about one nanometer of wavelength change in a direction parallel to the spectral axis. Accordingly, if a dye spectrum peak (from a point source) has a width of 30 nm (FWHM), it should extend over about 30 pixels on the detector. However, the FWHM of 30 nm from a point source, should be convolved with the spectral width of the well, about 40 nm, to broaden the peak from about 30 nm to 70 nm.

Example 11

Exemplary Adjustment of Optical Effects by Processing Image Data

This example describes exemplary potential advantages of processing image data via algorithms to correct for optical distortions and/or to provide software-level wavelength filtering.

Software algorithms for correcting image distortions can allow the optical design of the imaging system to be relaxed (a loser tolerance) such that the system is smaller and/or cheaper. Generally, software corrections are cheaper than hardware (optics) corrections.

The following relationships can be relevant in considering hardware versus software corrections of image distortion. (A) Spherical aberration is proportional to $(1/f\#)^3$. (B) Coma is proportional to $(1/f\#)^2 \times (FOV)$. (C) Astigmatism and field curvature are proportional to $(1/f\#) \times (FOV)^2$. (D) Distortion is proportional to $(FOV)^3$. FOV=field of view (physical dimension); f#=f number, which equals f/D (the collection angle of the optics is proportional to $1/f\#$); f=focal length; and D=effective diameter.

Distortions such as pincushion and barrel effects can come from imaging an object that is fairly large compared to the field of view of the optical system. This means that light rays from the edges of the object can enter into the optical system at a relatively large angle from the optical axis, and distortions can be a strong function of this angle. Software correction tools can allow design of a smaller and/or cheaper optical system, where the object size is large relative to the field of view, allowing the wells to be spaced as far as possible from one another. This can provide more room for dispersion and/or for more wells.

Further aspects of using algorithms to correct for optical distortion and/or to filter data according to wavelength are described in U.S. Provisional Patent Application Ser. No. 60/696,301, filed Jun. 30, 2005, which is incorporated herein by reference.

Example 12

Software-based Spectral Filters

This example describes exemplary aspects of software-based filters.

In exemplary embodiments, the pixel-to-wavelength relationship of the detector can be about one pixel/nm and the spectral range can be 100-150 nm. Software can be used to sum up the signal in groups of pixels, to simulate a narrow, medium, or wide band-pass filter, that is, to approximate, in software, a "virtual" filter corresponding to a hardware filter that could be positioned in the emission filter wheel of the imaging system. A virtual filter can be much cheaper than a hardware filter.

Example 13

Selected Embodiments

This example describes selected aspects and embodiments of the present teachings, presented as a series of numbered paragraphs.

1. A system for sample analysis, comprising: (A) a color separator configured to spectrally disperse light emitted from each sample of a two-dimensional sample array; and (B) a detector configured to detect and distinguish the dispersed light for each sample of the array.

2. The system of paragraph 1, further comprising a filter element configured to reduce selectively the amount of emitted visible light of relatively longer wavelengths that reaches the detector.

3. The system of paragraph 2, wherein the filter element is a short-pass filter.

4. The system of paragraph 1, further comprising a sample holder to hold the two-dimensional array of samples in a plurality of rows and columns, and wherein the rows, the columns, or both have a staggered configuration.

5. The system of paragraph 1, further comprising a sample holder to hold the two-dimensional array of samples in rows and columns arranged along orthogonal axes in an examination, wherein the sample holder is arranged relative to the color separator such that the color separator disperses emitted light spectrally to define a spectral axis of the examination area, and wherein the spectral axis is oblique to the each of the orthogonal axes.

6. The system of paragraph 1, further comprising a sample holder to hold the two-dimensional array of samples, the sample holder defining a plane and including a plurality of wells configured to dispose the samples in fluid isolation from one another, wherein the wells are elongate in the plane to define a long axis, and wherein the wells have a greater spacing from each other transverse to the long axis than parallel to the long axis.

7. The system of paragraph 1, wherein the color separator disperses the emitted light for each sample into a plurality of spectral components, and wherein the detector includes an array of sensor elements, the system further comprising a controller in communication with the detector and configured to relate signals from the sensor elements to particular samples and spectral components.

8. The system of paragraph 1, further comprising a controller configured to receive data corresponding to an image of the sample array detected by the detector, the controller including an algorithm configured to manipulate the data such that optical distortion of the sample array in the image is reduced.

9. The system of paragraph 8, wherein the algorithm is configured to stretch the image diagonally, curve the image, or both.

10. The system of paragraph 8, wherein the algorithm uses a polynomial function to control how much the image is modified.

11. The system of paragraph 1, wherein the detector is configured such that nondispersed light emitted from one or more of the samples can be detected by the detector concurrently with dispersed light from the samples.

12. The system of paragraph 11, wherein the nondispersed light is emitted from at least one row or column of samples dispersed adjacent a perimeter of the sample array.

13. The system of paragraph 11, wherein the detector detects positional information about the nondispersed light, further comprising a controller configured to use the positional information as a reference for relating dispersed light to particular samples and/or spectral components.

14. The system of paragraph 1, further comprising a light source configured to produce light that can be directed onto a two-dimensional array of samples in a manner capable of producing emitted light from each sample of the array.

15. The system of paragraph 14, further comprising an optical relay structure, wherein the light source includes a plurality of light sources, and wherein the optical relay structure is configured to direct light from each light source onto a different subset of samples within the array.

16. The system of paragraph 15, the two-dimensional array of samples including a plurality of rows, wherein the optical relay structure is configured to direct light from each light source onto a different subset of the rows.

17. The system of paragraph 15, wherein the optical relay structure is configured to direct light from each light source selectively onto only one row.

18. The system of paragraph 15, further comprising a controller in communication with the plurality of light sources, wherein the controller is configured to operate the light sources electronically for serial illumination of portions of the sample array.

19. A system for sample analysis, comprising: (a) an examination area including a two-dimensional array of examination sites for samples; (b) a light detector for imaging; and (c) an optical relay structure that spectrally disperses light emitted from luminophores disposed in the two-dimensional array of examination sites into a corresponding two-dimensional array of spectra directed concurrently onto the light detector, the optical relay structure including one or more filters disposed in an optical path between the examination sites and the light detector and configured to substantially truncate opposing ends of each spectrum by filtering the emitted light.

20. The system of paragraph 19, wherein the one or more filters include a short-pass and a long-pass filter.

21. The system of paragraph 19, wherein each filter substantially exclusively receives emitted light relative to excitation light.

22. A system for sample analysis, comprising: (a) an examination area including a two-dimensional array of examination sites for samples; (b) a light detector for imaging; and (c) an optical relay structure that spectrally disperses light emitted from luminophores disposed in the two-dimensional array of examination sites into a corresponding two-dimensional array of spectra directed concurrently onto the light detector such that the spectra would be substantially overlapping if not filtered, the optical relay structure including one or more filters disposed in an optical path between the examination sites and the light detector and configured to truncate each spectrum by filtering the emitted light such that there is a substantial reduction in crosstalk between adjacent spectra.

23. The system of paragraph 22, wherein the optical relay structure directs the two-dimensional array of spectra onto the light detector in a collectively nonoverlapping relation to nondispersed light from the array of examination sites.

24. The system of paragraph 22, wherein at least one of the one or more filters selectively restricts passage of light of relatively longer wavelengths, of relatively shorter wavelengths, or both.

25. The system of paragraph 22, wherein the one or more filters include a short-pass filter and a long-pass filter such that each spectrum is truncated at opposing ends of the spectrum.

26. The system of paragraph 25, wherein the one or more filters selectively restrict passage of light with a wavelength of less than about 500 nm and greater than about 650 nm.

27. The system of paragraph 22, further comprising a sample holder including wells, the sample holder being configured to be received in the examination area such that the wells are disposed in the examination sites.

28. The system of paragraph 27, wherein the sample holder includes at least one sealing element configured to seal each well individually after the well receives a sample.

29. The system of paragraph 22, further comprising a thermal control system operatively coupled to the examination area and configured to thermally regulate the examination area.

30. The system of paragraph 29, wherein the thermal control system is configured to thermally cycle the examination area repetitively in an automated manner.

31. The system of paragraph 22, further comprising a light source that illuminates each of the examination sites concurrently with excitation light.

32. The system of paragraph 31, wherein the light source includes a light-emitting diode.

33. The system of paragraph 22, wherein the spectra of the array each are of the same diffraction order.

34. A method of sample analysis, comprising: (a) disposing samples in a two-dimensional array of examination sites, each sample including one or more luminophores; (b) illuminating the samples such that the one or more luminophores of each sample emit light; (c) dispersing the emitted light of the samples concurrently into a corresponding two-dimensional array of spectra that are collectively spaced from nondispersed light from the examination sites and that would be overlapping if not filtered; (d) filtering the emitted light to substantially reduce crosstalk between adjacent spectra disposed end to end, by truncating each spectrum; (e) directing the array of spectra to a light detector such that each spectrum of the array falls onto the light detector at the same time; and (f) detecting an image of the array of spectra with the light detector.

35. The method of paragraph 34, wherein the step of disposing includes a step of disposing samples including reagents for nucleic acid amplification.

36. The method of paragraph 34, wherein the step of disposing includes a step of disposing a plurality of samples each including substantially the same set of one or more luminophores.

37. The method of paragraph 34, wherein the step of illuminating includes a step of illuminating each of the samples concurrently with a light-emitting diode.

38. The method of paragraph 34, wherein the step of dispersing is performed after the step of filtering.

39. The method of paragraph 34, wherein the step of filtering results in truncating opposing ends of each spectrum.

40. The method of paragraph 34, wherein the step of detecting includes a step of detecting a change, if any, in each spectrum over time.

41. The method of paragraph 34, wherein the step of detecting includes a step of obtaining image data corresponding to the image detected, further comprising a step of processing the image data according to pre-assigned regions of a detection area to obtain spectral data for each individual sample.

The disclosure set forth above can encompass multiple distinct inventions with independent utility. Although each of these inventions has been disclosed in its preferred form(s), the specific embodiments thereof as disclosed and illustrated herein are not to be considered in a limiting sense, because numerous variations are possible. The subject matter of the inventions includes all novel and nonobvious combinations and subcombinations of the various elements, features, functions, and/or properties disclosed herein. The following claims particularly point out certain combinations and subcombinations regarded as novel and nonobvious. Inventions embodied in other combinations and subcombinations of features, functions, elements, and/or properties can be claimed in applications claiming priority from this or a related application. Such claims, whether directed to a different invention or to the same invention, and whether broader, narrower, equal, or different in scope to the original claims, also are regarded as included within the subject matter of the inventions of the present disclosure.

What we claim:

1. A system for sample analysis, comprising:
   an examination area including a two-dimensional array of examination sites;
   a light detector for imaging;
   an optical relay structure that spectrally disperses light received from the examination sites into a corresponding two-dimensional array of spectra directed concurrently onto the light detector in a collectively nonoverlapping relation wherein the optical relay structure includes one or more filters that truncate a portion of each spectra to substantially reduce crosstalk between the spectra of the two-dimensional array when directed concurrently onto the light detector; and
   a thermal control system operatively coupled to the examination area for regulating a temperature thereof.

2. A system for sample analysis, comprising:
   an examination area including a two-dimensional array of examination sites;
   a light detector for imaging;
   a controller operatively coupled to the light detector and configured to process image data collected by the light detector to correct for optical distortion in the image data;
   an optical relay structure that spectrally disperses light received from the examination sites into a corresponding two-dimensional array of spectra directed concurrently onto the light detector in a collectively nonoverlapping relation wherein the optical relay structure includes one or more filters that truncate a portion of each spectra to substantially reduce crosstalk between the spectra of the two-dimensional array when directed concurrently onto the light detector; and
   a thermal control system operatively coupled to the examination area for regulating a temperature thereof.

3. The system of claim 1 or 2, further comprising a system controller, wherein the thermal control system is operatively coupled to the system controller for automated thermal control of the examination area.

4. The system of claim 1 or 2, wherein the thermal control system is configured to repetitively follow a thermal profile in an automated manner.

5. The system of claim 1 or 2, wherein the thermal control system includes a heater and a thermally conductive member operatively coupled to the heater, further comprising a sample holder having wells and configured to be disposed in the examination area such that the wells are disposed in the examination sites and the sample holder is in contact with the conductive member.

6. The system of claim 5, wherein the conductive member and the sample holder have complementary structure that restricts lateral movement of the sample holder when the sample holder is disposed in the examination area.

7. The system of claim 6, wherein the complementary structure includes one or more projections of the conductive member that are configured to be received in one or more openings of the sample holder.

8. The system of claim 1 or 2, further comprising a sample holder having wells and configured to be disposed in the examination area such that the wells are disposed in the examination sites, wherein the wells have a staggered arrangement.

9. The system of claim 8, wherein the wells are disposed along a set of spaced parallel lines with a well-to-well spacing within each line, and wherein every other line of wells is offset along its line by about one-half the well-to-well spacing.

10. The system of claim 1 or 2, further comprising a sample holder having wells and configured to be disposed in the examination area such that the wells are disposed in the examination sites, wherein each well is at least about one millimeter in diameter.

11. The system of claim 1 or 2, further comprising a sample holder having wells and configured to be disposed in the examination area such that the wells are disposed in the examination sites, wherein each well has a capacity of at least about 100 nanoliters.

12. A method of sample analysis, comprising:
   obtaining a two-dimensional array of samples for performing amplification of nucleic acids;
   cycling the samples thermally through a plurality of cycles;
   illuminating each sample of the array concurrently such that the samples emit light;
   directing dispersed light from each sample through at least one filter to a detection area such that a corresponding two-dimensional array of spectra falls concurrently onto the detection area and a portion of each spectra is truncated at the detector, wherein each spectra of the array of the spectra is non-overlapping with the remaining spectra of the array of the spectra;
   monitoring the two-dimensional array of spectra over time; and
   determining an aspect of one or more of the samples based on a measurement of the corresponding two-dimensional array of spectra.

* * * * *